US008329653B2

(12) United States Patent
Mehlen et al.

(10) Patent No.: US 8,329,653 B2
(45) Date of Patent: Dec. 11, 2012

(54) COMPOSITIONS AND METHODS FOR SUPPRESSION OF AMYLOID PLAQUE FORMATION ASSOCIATED WITH NEURODEGENERATIVE DISORDERS

(75) Inventors: Patrick Mehlen, Serezin-du-Rhone (FR); Dale E. Bredesen, Novato, CA (US); Filipe Calheiros-Lourenco, Lyons (FR); Veronica Galvan, Novato, CA (US)

(73) Assignees: Buck Institute for Age Research, Novato, CA (US); Centre National de la Recherche Scientifique, Paris (FR)

( * ) Notice: Subject to any disclaimer, the term of this patent is extended or adjusted under 35 U.S.C. 154(b) by 587 days.

(21) Appl. No.: 12/296,859

(22) PCT Filed: Apr. 16, 2007

(86) PCT No.: PCT/US2007/009394
§ 371 (c)(1),
(2), (4) Date: Jan. 26, 2009

(87) PCT Pub. No.: WO2007/120912
PCT Pub. Date: Oct. 25, 2007

(65) Prior Publication Data
US 2009/0181881 A1      Jul. 16, 2009

Related U.S. Application Data

(60) Provisional application No. 60/792,369, filed on Apr. 14, 2006.

(51) Int. Cl.
*A61K 9/127*      (2006.01)
*A61K 38/17*      (2006.01)

(52) U.S. Cl. ....... 514/17.7; 424/450; 514/1.1; 514/17.8; 514/20.9; 514/21.2; 530/350; 530/359; 530/395; 530/402

(58) Field of Classification Search ................ None
See application file for complete search history.

(56) References Cited

U.S. PATENT DOCUMENTS

| | | | |
|---|---|---|---|
| 5,268,164 A | 12/1993 | Kozarich et al. | |
| 5,420,109 A | 5/1995 | Suto et al. | |
| 5,506,206 A | 4/1996 | Kozarich et al. | |
| 5,565,331 A * | 10/1996 | Tessier-Lavigne et al. | 435/69.1 |
| 5,686,416 A | 11/1997 | Kozarich et al. | |
| 5,752,515 A | 5/1998 | Jolesz et al. | |
| 5,854,204 A | 12/1998 | Findeis et al. | |
| 2003/0162695 A1* | 8/2003 | Schatzberg et al. | 514/8 |
| 2004/0204354 A1* | 10/2004 | Nelson et al. | 514/12 |
| 2005/0014680 A1* | 1/2005 | Crabtree et al. | 514/3 |
| 2005/0124533 A1 | 6/2005 | Schatzberg et al. | |

FOREIGN PATENT DOCUMENTS

| | | | |
|---|---|---|---|
| WO | WO-97/40064 A1 | | 10/1997 |
| WO | WO 02/24142 | * | 3/2002 |
| WO | WO-2006/019904 A1 | | 2/2006 |

OTHER PUBLICATIONS

Kreuter et al., J. Drug Targeting, vol. 10 (4), 2002, pp. 317-325.*
Guo et al., PNAS, vol. 101 (25), 2004, pp. 9205-9210.*
Tessier-Lavigne et al., vol. 274 (5290), 1996, pp. 1123-1133.*
Ando et al., Phosphorylation-dependent regulation of the interaction of amyloid precursor protein with Fe65 affects the production of beta-amyloid, J. Biol. Chem., 276:40353-61 (2001).
Bashaw et al., Chimeric axon guidance receptors: the cytoplasmic domains of slit and netrin receptors specify attraction versus repulsion, Cell, 97:917-26 (1999).
Brem et al., Interstitial chemotherapy with drug polymer implants for the treatment of recurrent gliomas, J. Neurosurg., 74:441-6 (1991).
Cao et al., A transcriptionally [correction of transcriptively] active complex of APP with Fe65 and histone acetyltransferase Tip60, Science, 293:115-20 (2001).
Cao et al., Dissection of amyloid-beta precursor protein-dependent transcriptional transactivation, J. Biol. Chem., 279:24601-11 (2004).
Colamarino et al., The axonal chemoattractant netrin-1 is also a chemorepellent for trochlear motor axons, Cell, 81:621-9 (1995).
Corset et al., Netrin-1-mediated axon outgrowth and cAMP production requires interaction with adenosine A2b receptor, Nature, 407:747-50 (2000).
De La Torre et al., Turning of retinal growth cones in a netrin-1 gradient mediated by the netrin receptor DCC, Neuron, 19:1211-24 (1997).
Filmore, Breaching the blood-brain barrier, Modern Drug Discovery, 5:22-24, 27 (2002).
Forcet et al., Netrin-1-mediated axon outgrowth requires deleted in colorectal cancer-dependent MAPK activation, Nature, 417:443-7 (2002).
Forcet et al., The dependence receptor DCC (deleted in colorectal cancer) defines an alternative mechanism for caspase activation, Proc. Natl. Acad. Sci. USA, 98:3416-21 (2001).
Galvan et al., Caspase cleavage of members of the amyloid precursor family of proteins, J. Neurochem., 82:283-94 (2002).
Galvan et al., Reversal of Alzheimer's-like pathology and behavior in human APP transgenic mice by mutation of Asp664, Proc. Natl. Acad. Sci. USA, 103:7130-5 (2006).
Heber et al., Mice with combined gene knock-outs reveal essential and partially redundant functions of amyloid precursor protein family members, J. Neurosci., 20:7951-63 (2000).
Hedgecock et al., The unc-5, unc-6, and unc-40 genes guide circumferential migrations of pioneer axons and mesodermal cells on the epidermis in *C. elegans*, Neuron., 4:61-85 (1990).
Homayouni et al., Disabled-1 binds to the cytoplasmic domain of amyloid precursor-like protein 1, J. Neurosci., 19:7507-15 (1999).
International Preliminary Report on Patentability for corresponding International Application No. PCT/US2007/009394, dated Oct. 14, 2008.

(Continued)

*Primary Examiner* — Jeffrey Stucker
*Assistant Examiner* — Stephen Gucker
(74) *Attorney, Agent, or Firm* — Tom Hunter; Weaver Austin Villeneuve & Sampson LLP

(57) ABSTRACT

The invention provides methods and compositions for reducing or inhibiting net beta-amyloid peptide production and/or amyloid plaque formation. The methods and compositions involve administering a netrin-1 polypeptide or netrin-1 therapeutic to a subject in need thereof.

17 Claims, 15 Drawing Sheets

OTHER PUBLICATIONS

International Search Report and Written Opinion for corresponding International Application No. PCT/US2007/009394, dated Feb. 6, 2008.

Jones et al., Blood-brain barrier transport of therapeutics via receptor-mediation, Pharm. Res., 24:1759-71 (2007).

Keino-Masu et al., Deleted in Colorectal Cancer (DCC) encodes a netrin receptor, Cell, 87:175-85 (1996).

Kennedy et al., Netrins are diffusible chemotropic factors for commissural axons in the embryonic spinal cord, Cell, 78:425-35 (1994).

Kimberly et al., The intracellular domain of the beta-amyloid precursor protein is stabilized by Fe65 and translocates to the nucleus in a notch-like manner, J. Biol. Chem., 276:40288-92 (2001).

Kreuter et al., Passage of peptides through the blood-brain barrier with colloidal polymer particles (nanoparticles), Brain Res., 674:171-4 (1995).

Lauderdale et al., Axon tracts correlate with netrin-1a expression in the zebrafish embryo, Mol. Cell Neurosci., 9:293-313 (1997).

Lu et al., A second cytotoxic proteolytic peptide derived from amyloid beta-protein precursor, Nat. Med., 6:397-404 (2000).

Lu et al., Amyloid beta protein toxicity mediated by the formation of amyloid-beta protein precursor complexes, Ann. Neurol., 54:781-9 (2003).

Mehlen et al., The DCC gene product induces apoptosis by a mechanism requiring receptor proteolysis, Nature, 395:801-4 (1998).

Meyerhardt et al., Netrin-1: interaction with deleted in colorectal cancer (DCC) and alterations in brain tumors and neuroblastomas, Cell Growth Differ., 10:35-42 (1999).

Otto et al., Basic FGF reverses chemical and morphological deficits in the nigrostriatal system of MPTP-treated mice, J. Neurosci., 10:1912-21 (1990).

Otto et al., Basic fibroblast growth factor and nerve growth factor administered in gel foam rescue medial septal neurons after fimbria fornix transection, J. Neurosci. Res., 22:83-91 (1989).

Puschel, Divergent properties of mouse netrins, Mech. Dev., 83:65-75 (1999).

Serafini et al., Netrin-1 is required for commissural axon guidance in the developing vertebrate nervous system, Cell, 87:1001-14 (1996).

Serafini et al., The netrins define a family of axon outgrowth-promoting proteins homologous to *C. elegans* UNC-6, Cell, 78:409-24 (1994).

Shin et al., Transferrin-antibody fusion proteins are effective in brain targeting, Proc. Natl. Acad. Sci. USA, 92:2820-4 (1995).

Skarnes et al., Capturing genes encoding membrane and secreted proteins important for mouse development, Proc. Natl. Acad. Sci. USA, 92:6592-6 (1995).

Strahle et al., Expression and regulation of a netrin homologue in the zebrafish embryo, Mech. Dev., 62:147-60 (1997).

Tanikawa et al., p53RDL1 regulates p53-dependent apoptosis, Nat. Cell Biol., 5:216-23 (2003).

Trommsdorff et al., Interaction of cytosolic adaptor proteins with neuronal apolipoprotein E receptors and the amyloid precursor protein, J. Biol. Chem., 273:33556-60 (1998).

Van Raay et al., The NTN2L gene encoding a novel human netrin maps to the autosomal dominant polycystic kidney disease region on chromosome 16p13.3, Genomics, 41:279-82 (1997).

Von Rotz et al., The APP intracellular domain forms nuclear multiprotein complexes and regulates the transcription of its own precursor, J. Cell Sci., 117:4435-48 (2004).

Wang et al., Netrin-3, a mouse homolog of human NTN2L, is highly expressed in sensory ganglia and shows differential binding to netrin receptors, J. Neurosci., 19:4938-47 (1999).

Winberg et al., Genetic analysis of the mechanisms controlling target selection: complementary and combinatorial functions of netrins, semaphorins, and IgCAMs, Cell, 93:581-91 (1998).

\* cited by examiner c = 0.67

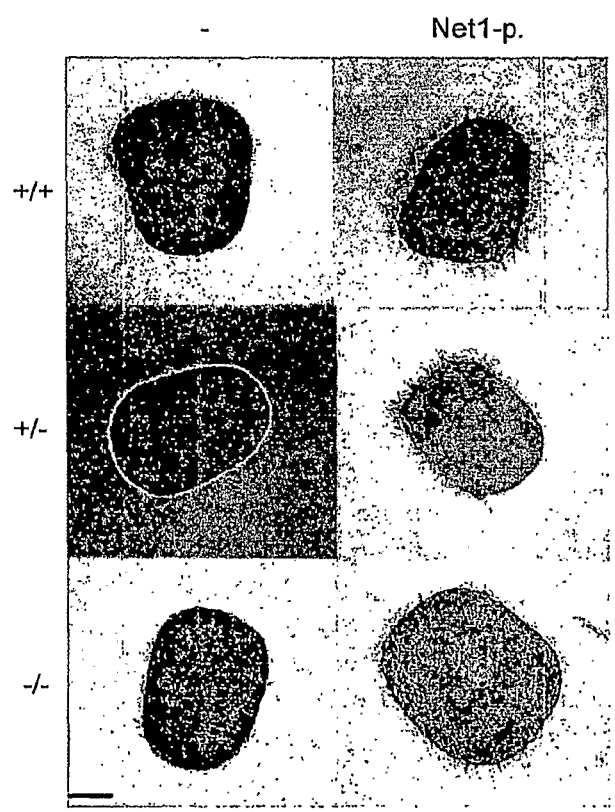
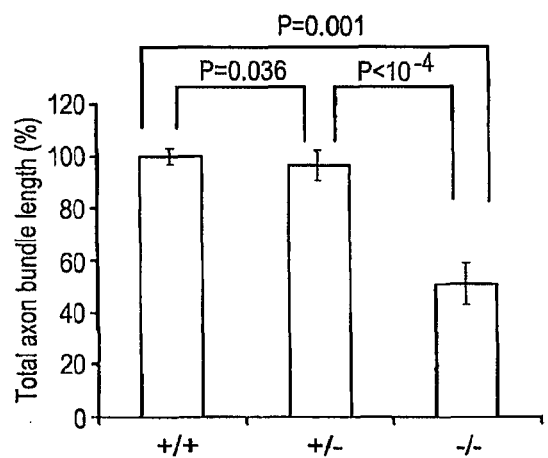
FIG. 5A  FIG. 5B

```
 01 mmravweala alaaavaclvg avrggpglsm fagqaaqpdp csdenghprr cipdfvnaaf
 61 gkdvrvsstc grpparycvv sergeerlrs chlcnasdpk kahppafltd lnnphnltcw
121 qsenylqfph nvtltlslgk kfevtyvslq fcsprpesma iyksmdygrt wvpfqfystq
181 crkmynrphr apitkqneqe avctdshtdm rplsggliaf stldgrpsah dfdnspvlqd
241 wvtatdirva fsrlhtfgde neddselard syfyavsdlq vggrckcngh aarcvrdrtd
301 slvcdcrhnt agpecdrckp fhydrpwqra tareanecva cncnlharrc rfnmelykls
361 grksggvcln crhntagrhc hyckegyyrd mgkpithrka ckacdchpvg aagktcnqtt
421 gqcpckdgvt gitcnrcakg yqqsrspiap cikipvappt taassveepe dcdsyckask
481 gklkinmkky ckkdyavqih ilkadkagdw wkftvniisv ykqgtsrirr gdqslwirsr
541 diackcpkik plkkylllgn aedspdqsgi vadksslviq wrdtwarrlr kfqqrekkgk
601 ckka
```

FIG. 7A

```
   1 agcttcgggg gcgagcgctc gtgtgtgtga gtgcgcgccg gccagcgcgc cttctgcggc
  61 aggcggacag atcctcggcg cggcagggcc ggggcaagct ggacgcagca tgatgcgcgc
 121 agtgtgggag gcgctggcgg cgctggcggc ggtggcgtgc ctggtgggcg cggtgcgcgg
 181 cgggcccggg ctcagcatgt tcgcggggcca ggcggcgcag cccgatccct gctcggacga
 241 gaacggccac ccgcgccgct gcatcccgga ctttgtcaat gcggccttcg gcaaggacgt
 301 gcgcgtgtcc agcacctgcg gccggccccc ggcgcgctac tgcgtggtga gcgagcgcgg
 361 cgaggagcgg ctgcgctcgt gccacctctg caacgcgtcc gaccccaaga aggcgcaccc
 421 gcccgccttc ctcaccgacc tcaacaaccc gcacaacctg acgtgctggc agtccgagaa
 481 ctacctgcag ttcccgcaca acgtcacgct cacactgtcc ctcggcaaga agttcgaagt
 541 gacctacgtg agcctgcagt tctgctcgcc gcggcccgag tccatggcca tctacaagtc
 601 catggactac gggcgcacgt gggtgccctt ccagttctac tccacgcagt gccgcaagat
 661 gtacaaccgg ccgcaccgcg cgcccatcac caagcagaac gagcaggagg ccgtgtgcac
 721 cgactcgcac accgacatgc gcccgctctc gggcggcctc atcgccttca gcacgctgga
 781 cgggcggccc tcggcgcacg acttcgacaa ctcgcccgtg ctgcaggact gggtcacggc
 841 cacagacatc cgcgtggcct tcagccgcct gcacacgttc ggcgacgaga acgaggacga
 901 ctcggagctg gcgcgcgact cgtacttcta cgcggtgtcc gacctgcagg tgggcggccg
 961 gtgcaagtgc aacggccacg cggcccgctg cgtgcgcgac cgcaccgaca gcctggtgtg
1021 cgactgcagg cacaacacgg ccggcccgga gtgcgaccgc tgcaagccct ccactacga
1081 ccggccctgg cagcgcgcca gcccgcga agccaacgag tgcgtggcct gtaactgcaa
1141 cctgcatgcc cggcgctgcc gcttcaacat ggagctctac aagctttcgg ggcgcaagag
1201 cggaggtgtc tgcctcaact gtcgccacaa caccgccggc cgccactgcc attactgcaa
1261 ggagggctac taccgcgaca tgggcaagcc catcacccac cggaaggcct gcaaagcctg
1321 tgattgccac cctgtgggtg ctgctggcaa aacctgcaac caaaccaccg gccagtgtcc
1381 ctgcaaggac ggcgtgacgg gtatcacctg caaccgctgc gccaaaggct accagcagag
1441 ccgctctccc atcgcccct gcataaagat ccctgtagcg ccgccgacga ctgcagccag
1501 cagcgtggag gagcctgaag actgcgattc ctactgcaag gcctccaagg ggaagctgaa
1561 gattaacatg aaaaagtact gcaagaagga ctatgccgtc cagatccaca tcctgaaggc
1621 ggacaaggcg ggggactggt ggaagttcac ggtgaacatc atctccgtgt ataagcaggg
1681 cacgagccgc atccgccgcg gtgaccagag cctgtggatc cgctcgcggg acatcgcctg
1741 caagtgtccc aaaatcaagc ccctcaagaa gtacctgctg ctgggcaacg cggaggactc
1801 tccggaccag agcggcatcg tggccgataa aagcagcctg gtgatccagt ggcgggacac
1861 gtgggcgcgg cggctgcgca agttccagca gcgtgagaag aagggcaagt gcaagaaggc
1921 ctagcgccga ggcagcgggc gggcgggccg ggcgggcccg agggcggggc gagcgagacg
1981 gcgcttggc
```

COMPOSITIONS AND METHODS FOR SUPPRESSION OF AMYLOID PLAQUE FORMATION ASSOCIATED WITH NEURODEGENERATIVE DISORDERS

This application is the U.S. national stage of international patent application PCT/US2007/009394, filed Apr. 16, 2007, which claims benefit of and priority to U.S. Provisional Application No. 60/792,369, filed on Apr. 14, 2006.

The invention relates generally to methods for inhibiting net amyloid-β (Aβ) peptide production in the central nervous system (CNS) and, more specifically, to methods for treating or preventing neurodegenerative diseases, such as Alzheimer's disease, using netrin-1 peptides.

BACKGROUND OF THE INVENTION

Alzheimer's disease (AD), the most common form of dementia, is a progressive neurodegenerative disorder characterized by extracellular deposits of A peptide in senile plaques, intraneuronal neurofibrillary tangles, synapse loss, and cognitive decline. It is widely believed that the accumulation of Aβ, a small peptide with a high propensity to form oligomers and aggregates, is central to the pathogenesis of AD. APP is cleaved by proteases including α,β, and γ-secretases, generating amyloid-β (Aβ) peptide, the main component of the amyloid plaques that are associated with Alzheimer's disease.

Aβ derives from the proteolytic cleavage of the transmembrane protein, APP. Although a considerable amount is known about interacting proteins and processing events for APP, the physiological role(s) of APP and its related family members, APLP1 and APLP2 (amyloid precursor-like proteins 1 and 2), is still poorly understood. APP has been proposed to function in cell adhesion and motility, as well as synaptic transmission and plasticity. The cloning and characterization of APP revealed that it possesses many features reminiscent of a membrane-anchored receptor. Compatible with this notion, APP was suggested to function as a single transmembrane G-protein coupled receptor. However, to date, no clear candidate has emerged as the major ligand triggering APP mediated signal transduction (although several molecules have been shown to bind APP, such as collagen (types I and IV), heparan sulfate proteoglycan, laminin, and glypican)—at least in part because the signal transduction mediated by APP remains incompletely understood.

Thus, there is a need for identification of molecules that bind APP and modulate APP signaling and AB peptide production. The present invention meets this need and provides related advantages.

SUMMARY OF THE INVENTION

The invention provides a method for reducing or inhibiting net beta-amyloid peptide production and amyloid plaque formation associated with Alzheimer's Disease by administering to a subject an amount of a netrin-1 polypeptide, wherein the netrin-1 polypeptide comprises an amino acid sequence that a) binds to a naturally occurring APP protein and b) inhibits AB peptide production. A netrin-1 polypeptide has an amino acid sequence sufficient for specific binding of the netrin-1 polypeptide to the APP protein. A netrin-1 polypeptide can mimic netrin-1-mediated signal transduction by altering the localization, protein-protein binding and/or enzymatic activity of an intracellular protein involved in an APP signal pathway. The invention also provides a method for reducing or inhibiting amyloid plaque formation associated with Alzheimer's Disease by administering to a subject an amount of a netrin-1 therapeutic, wherein the netrin-1 therapeutic comprises an amino acid sequence that a) binds to a naturally occurring APP protein and b) inhibits AB peptide production.

BRIEF DESCRIPTION OF THE DRAWINGS

FIG. 5. APP is required for netrin-1-mediated cortical axon outgrowth. Cortical explants were dissected out from E13.5 wild-type or APP mutant embryos as indicated in upper right panel and cultured in collagen in the presence or not of 375 ng/ml of netrin-1. a, Representative images of axon outgrowth in the different tested conditions are shown. b, The total number of explants that were quantified from 5 distinct experiments varied from 8-12 per tested condition. Values shown are means±SEM. Scale bars: 200 µm. A Kruskall-Wallis test was used comparing the overall condition, p=0.001. A Mann-Whitney test was also used to compare +/+ versus +/− (p=0.036), and +/− versus −/− (p<10-4).

FIG. 7. Shows in panel (A) the amino acid sequence of human netrin-1 (SEQ ID NO:1) and in panel (B) the mRNA sequence of human netrin-1 (SEQ ID NO:2).

DETAILED DESCRIPTION OF THE INVENTION

Figure 1A:
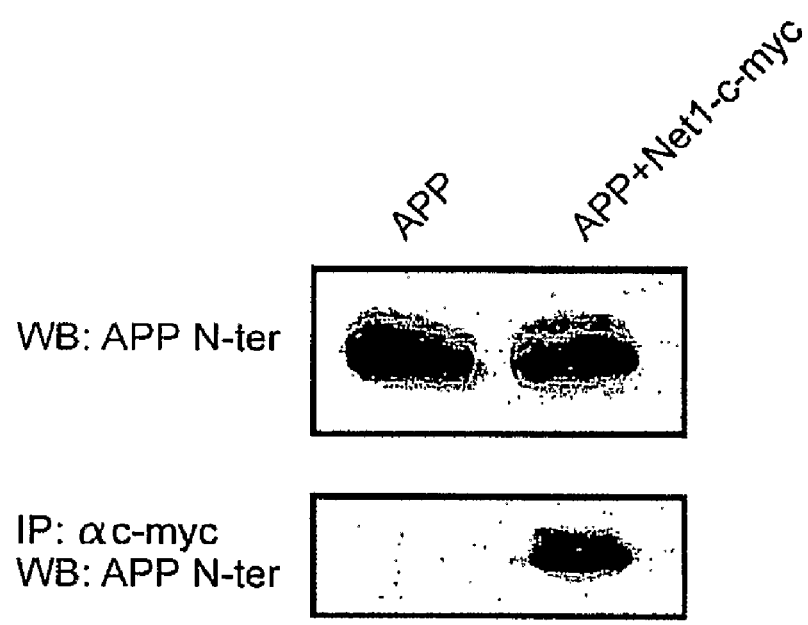
FIG. 1. Netrin-1 interacts with APP and APLP1. a-c, HEK293T cells were transiently transfected with myc-tagged netrin-1 and/or APP and/or TrkC. Either conditioned medium (b) or cell lysate (a,c) was utilized for immunoprecipitation, using either an anti-c-myc antibody (for netrin) (a,b), an anti-N-terminal APP antibody (c) or an anti-TrkC antibody (c). Immunoprecipitations were subjected to polyacrylamide gel electrophoresis, transferred, and probed with antibodies raised against N-terminal APP (a,b) or netrin-1 (c). d, HEK293T cells were transfected with netrin-1 expressing construct or not and endogenous APP was, after c-myc (netrin-1) pull-down, revealed using an anti-C-terminal APP antibody. e, Colocalization of 5A3/1G7 (APP extracellular domain) with netrin-1 in growth cones of primary cortical neurons. Primary cultures of neurons from DBA/2J embryos were fixed in 4% PFA and stained with 5A3/1G7 and anti-netrin 64 or with mouse and rabbit IgGs followed by Alexa568- and Alexa488-conjugated anti-mouse and anti-rabbit secondary antibodies respectively. Stacks of images (z step=0.25 mm) were acquired with a laser scanning confocal microscope (Nikon PCM-2000) using a 100× objective and a 2.7 digital zoom, collected using SimplePCI software (Compix Inc., Lake Oswego, Oreg.) and processed in an SGI Octane R12 computer running Bitplane's Advanced Imaging Software suite. Analysis of colocalization was done using the Coloc algorithm in Imaris Bitplane. The Pearson correlation coefficient of channel A (green) and channel B (red) inside the colocalized region (c) was used as a measure of the degree of colocalization 36. Panels shown: Net1 (netrin-1); APP; merge; Coloc (colocalization channel); IgG's (mouse and rabbit IgGs). f-g, Cortex from E16.5 mouse embryos were collected and semi-dissociated and cells lysates were submitted to immunoprecipitation using anti-APP (C-terminal or N-terminal), anti-TrkC or anti-p75$^{ntr}$ antibody (f) or anti-netrin-1 (anti-mouse netrin-1: anti-mNet1), anti-bFGF antibody or respective irrelevant IgGs (g) for the pull-down. Immunoblot were then performed using either APP, p75$^{ntr}$ or TrkC antibody (f) or netrin-1 or bFGF antibody (g). h-i, HEK293T cells were transiently transfected with myc-tagged netrin-1, netrin-2 or ΔC netrin-1 (net (V,VI)), netrin G1, and APP, Flag-tagged APLP1 or APLP2. Cell lysate was utilized for immunoprecipitation, using either an anti-c-myc antibody (for netrin) (i) or FlagM2 antibody (for APLP1 and APLP2) (h). In a-d,h,i, the upper panels show expression of the proteins prior to pull-down, and the lower panel(s) is (are) after pull-down. In f,g, all panels show expression of the proteins after pull-down (j) 150 ng of recombinant αAPPs was added to increasing concentrations of purified c-myc-tagged netrin-1 in 1 ml reaction buffer. Netrin-1 pull-down was performed (with anti-c-myc), and the concentration of αAPPs pulled down with netrin-1 was quantified after Western blotting, using anti-APP antibody and NIH image software. A similar analysis was performed with DCC-EC. Bottom panels: input of αAPPs and DCC-EC shown by Western blot. k, An Elisa assay was developed to determine the KdAPP/netrin. 2.5 μg/ml of αAPPs protein was coated in 96-wells plate and various netrin-1 concentrations were added. Similar experiment was performed using the pair APP/bFGF or the pair APLP2/netrin-1. Quantification of the interaction is indicated here by the measurement of the optic density (intensity). Kd determination was derived from a simulated Scatchard plot (Bound/Estimated Free=f(Bound)).

This invention is based, in part, on the discovery that netrin-1 functions as a ligand for APP, that it modulates APP signaling, and that it markedly inhibits net beta amyloid (Aβ) peptide production in vivo. In particular, the invention provides netrin-1 polypeptides and functional fragments thereof compete with Aβ peptide for binding to APP and effect the net production of Aβ peptide. Furthermore, because the netrin-1 polypeptides and functional fragments of the invention interact directly with Aβ peptide, they can affect the oligomerization and clearance of the Aβ peptide.

As disclosed herein, netrin-1 (i) decreases Aβ1-40 and Aβ1-42 concentrations in brain slices from Alzheimer-model in vivo; (ii) it interacts with Aβ peptide; (iii) displays a neurotrophic effect.

In one embodiment, the invention provides a method for reducing or inhibiting beta amyloid peptide production and amyloid plaque formation associated with Alzheimer's Disease comprising administering to a subject an amount of a netrin-1 polypeptide, wherein the netrin-1 polypeptide comprises an amino acid sequence that a) binds to a naturally occurring APP protein and b) inhibits Aβ peptide production.

Although the description of the invention references mainly Alzheimer's Disease, any neurodegenerative condition associated with beta amyloid plaque formation or Aβ peptide production is a candidate for therapy that encompasses the compositions and methods disclosed herein. In addition, conditions that known to overlap with Alzheimer's disease such that symptoms associated with Alzheimer's disease are present, for example, Lewy body dementia, can be targeted with the treatment methods provided by the present invention. Lewy bodies refer to abnormal structures within nerve cells of the brain and it is estimated that up to 40 percent of people with Alzheimer's have Lewy bodies in the neocortex. Cerebral amyloid angiopathy (CAA) refers to the deposition of β-amyloid in the media and adventitia of small- and mid-sized arteries (and less frequently, veins) of the cerebral cortex and the leptomeninges. It is a component of any disorder in which amyloid is deposited in the brain, and it is not associated with systemic amyloidosis.

Netrins comprise a family of structurally related secreted molecules involved in axon guidance. Axons sense netrins as either attractants or repellents, depending upon which netrin receptors are expressed on their growth cones (Hedgecock et al., 1990, Neuron 4:61-85; Serafini et al., 1994, Cell 78:409-424; Colamarino and Tessier Lavigne, (1995) Cell 81:621-629; Winberg et al., 1998, supra), or differences in the cellular signal transduction machinery (Bashaw and Goodman, 1999, Cell 97:917-926).

Netrin-1 has been identified in chicken (Serafini et al., 1994, supra), mouse (Serafini et al., 1996, Cell 87:1001-1014), *Xenopus* (de la Terre et al., 1997, Neuron 19:1211-1224), zebrafish (Lauderdale et al., 1997 Mo. Cell Neurosci. 9:293-313; Strahle et al., 1997, Mech. Dev. 62:147-160), and human (Meyerhardt et al., 1999, Cell Growth Differ. 10:35-42); netrin-2 in chicken (Serafini et al., 1994, supra); netrin-3 in human (NTN2L, Van Raay et al., 1997, Genomics 41:279-282) and mouse (Wang et al., 1999, J. Neurosci 19:4938-4947). Netrins 1,2 and 3 are all structurally related to the short arms of laminin γ chains, and contain a laminin VI domain and three epidermal growth factor-like (EGF-like) repeats similar to the laminin V domain (V-1, V-2 and V-3); they also contain a positively charged heparin-binding C-terminal domain termed "domain C" (Serafini et al., 1994, supra; Keino-Masu, 1996, Cell 87:175-185). The human netrin-1 amino acid sequence is known in the art (see, for example, Serafini et al., Cell 87 (6): 1001-1014 (1996)) and can be obtained, for example, from any of various public databases including whole genome databases such as those operated by The National Center for Biotechnology Information (NCBI) of the National Institutes of Health (NIH). For example, the netrein-1 amino acid sequence and corresponding nucleic acid sequence can be obtained from GenBank under accession number NM_004822 (mRNA) and NP_004813, Nov. 17, 2006.

Mutations in the netrin genes in *C. elegans* (unc-6) (Hedgecock et al., 1990, supra), *Drosophila* (NetA/B) (Winberg et al., 1998, Cell 93:581-591), and mouse (netrin-1) (Skarnes et al., 1995, Proc. Nat. Acad. Sci. USA 92:6592-6596; Serafini et al., 1996, supra) produce defects in axon guidance affecting circumferential and commissural growth. Studies in vitro show that netrin-1 can act from a distance within a collagen gel to cause the outgrowth of spinal cord axons; implicating chemoattraction as the mechanism of action of netrins (Kennedy et al., 1994, Cell 78:425-435). As described herein, Aβ peptide can inhibit netrin-1-dependent neurite outgrowth, and function as an anti-trophin.

In mouse and chicken, the RNA transcripts encoding the netrins are widely distributed throughout the organism (Wang et al., 1999, J. Neurosci. 19:4938-4947). Netrin RNAs are prominent in embryonic muscle and the bronchi of lung; transcripts are also present in the condensing mesenchyme of the limb and esophagus. However, netrin RNA location has been most extensively documented in the CNS. Netrin-1 is strongly expressed in the developing spinal cord, in the floorplate and the ventral ventricular zone (Serafini et al., 1996, supra; Wang et al. 1999, supra; Puschel, 1999, Mech. Dev. 83:65-75). Netrin-2 is expressed throughout the spinal cord and in the dorsal root ganglia, but not in the floor plate (Wang et al., 1999, supra). Netrin-3 is expressed more limitedly in the dorsal root ganglia and the motor column of the ventral spinal cord (Wang et al., 1999, supra; Puschel, 1999, supra).

As used herein, the term "netrin-1 polypeptide" refers to a polypeptide that encompasses a portion of the amino acid sequence of netrin-1 sufficient to confer one or more of the following activities: 1) binding to a naturally occurring APP protein; 2) markedly suppresses production of both Aβ 1-40 and Aβ 1-42; 3) interacting with Aβ peptide; and 4) modulating APP signaling. The term production in the context of Aβ peptide encompasses a decrease in Aβ peptide can be due to lower production, increased degradation, or both. A netrin-1 polypeptide can be substantially the same as the human polypeptide corresponding to the amino acid sequence as deposited, for example, under Genbank Accession number NP_004813, Nov. 17, 2006. The netrin-1 sequence can be accessed in the Genbank repository. Sequence information for known proteins is available from a variety of well known sources including, for example, user derived, public or private databases, subscription sources and on-line public or private sources. The term is intended to include conservative amino acid substitutions of the amino acid sequence shown in Minor modifications do not substantially affect the structure or activity of a netrin-1 polypeptide of the invention. Further, various molecules can be attached to a netrin-1 polypeptide and functional fragments thereof, including for example, other polypeptides, carbohydrates, lipids, detectable labels and cytotoxic or cytostatic agents. Such modifications are included within the definition of the term.

As used herein, the term "isolated" when used in reference to a polypeptide of the invention is intended to mean that the polypeptide is in a form that is relatively free from material that normally is associated with the nucleic acid or polypeptide in a cell, tissue or in a crude preparation. Therefore, an isolated polypeptide of the invention has been separated from one or more other components and is in a form that it is not normally found in nature. Generally, an isolated polypeptide will be in a substantially purified form, but also can include unpure preparations such as preparations that enrich for the polypeptide so long as some materials or components normally associated with the molecule have been removed.

As used herein, the term "polypeptide" is intended to mean two or more amino acids covalently bonded together. A polypeptide of the invention includes polypeptides having a several hundred or more amino acid residues, including full length netrin-1 having about 604 amino acids. A polypeptide of the invention also includes functional fragments of netrin-1. In general, the covalent bond between the two or more amino acid residues is an amide bond. However, the amino acids can be joined together by various other means known to those skilled in the peptide and chemical arts. Therefore, the term "polypeptide" is intended to include molecules which contain, in whole or in part, non-amide linkages between amino acids, amino acid analogs and mimetics. Similarly, the term also includes cyclic peptides and other conformationally constrained structures.

As used herein, the term "amino acid" is intended to mean both naturally occurring and non-naturally occurring amino acids as well as amino acid analogs and mimetics. Naturally occurring amino acids include the 20 (L)-amino acids utilized during polypeptide biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics a positively charged amino acid side chain similarly contains a positive charge moiety located in similar molecular space and having the same degree of mobility as the reference side chain. Mimetics also include constrained structures so as to maintain optimal spacing and charge interactions of the amino acid or of the amino acid functional groups.

Those skilled in the art know or can determine what structures constitute functionally equivalent amino acid analogs and amino acid mimetics. Specific examples of amino acid analogs and mimetics can be found described in, for example, Roberts and Vellaccio, *The Peptides: Analysis, Synthesis, Biology*, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, *Combinatorial Chemistry*, Eds. Wilson and Czarnik, Ch. 11, p. 235, John Wiley & Sons Inc., New York, N.Y. (1997), the entire book of which is incorporated herein by reference. Yet other examples include amino acids whose amide portion (and, therefore, the amide backbone of the resulting peptide) has been replaced, for example, by a sugar ring, steroid, benzodiazepine or carbo cycle. See, for instance, *Burger's Medicinal Chemistry and Drug Discovery*, Ed. Manfred E. Wolff, Ch. 15, pp. 619-620, John Wiley & Sons Inc., New York, N.Y. (1995), the entire book of which is incorporated herein by reference. Methods for synthesizing peptides, polypeptides, peptidomimetics and polypeptides are well known in the art (see, for example, U.S. Pat. No. 5,420,109; M. Bodanzsky, *Principles of Peptide Synthesis* (1 st ed. & 2d rev. ed.), Springer-Verlag, New York, N.Y. (1984 & 1993), see Chapter 7; Stewart and Young, *Solid Phase Peptide Synthesis*, (2d ed.), Pierce Chemical Co., Rockford, Ill. (1984), each of which is incorporated herein by reference).

Functional fragments of a netrin-1 polypeptide of the invention are additionally provided. The functional fragments include at least about ten contiguous amino acids of the netrin-1 amino acid sequence that exhibit substantially the same function of an intact netrin-1 polypeptide. Specific examples of netrin-1 polypeptide functional fragments include amino acid residues 25 through 60 of SEQ ID NO:1; amino acid residues 375 through 440 of SEQ ID NO:1; amino acid residues 425 through 460 of SEQ ID NO:1; and the C-terminal 50 amino acid residues of SEQ ID NO:1. A netrin-1 polypeptide encompasses an amino acid sequence sufficient for specific binding of the netrin-1 polypeptide to the APP protein.

A netrin-1 polypeptide or functional fragment thereof can mimic netrin-1-mediated signal transduction by altering the localization, protein-protein binding and/or enzymatic activity of an intracellular protein involved in an APP signal pathway. A netrin-1 polypeptide corresponding to these sequences will exhibit substantially the same activity as intact netrin-1 polypeptide. Such functional fragments can include, for example, a netrin-1 fragment corresponding to amino acid residues 25 through 60 of SEQ ID NO: 1; amino acid residues 375 through 440 of SEQ ID NO: 1; amino acid residues 425 through 460 of SEQ ID NO: 1; and the C-terminal 50 amino acid residues of SEQ ID NO: 1. A functional fragment of a netrin-1 polypeptide encompasses an amino acid sequence sufficient for specific binding of the netrin-1 polypeptide to the APP protein.

The present invention encompasses netrin-1 polypeptides and functional fragments thereof that have substantially the same amino acid sequence and consequently show a considerable degree, amount or extent of sequence identity when compared to reference netrin-1 sequence and therefore exhibit characteristics which are definitively recognizable or known as being derived from or related to the reference netrin-1 polypeptide or functional fragment. For example, an amino acid sequence which is substantially the same amino acid sequence as a netrin-1 polypeptide, including functional fragments thereof, refers to a sequence which exhibits characteristics that are definitively known or recognizable as being sufficiently related to human netrin-1 so as to fall within the classification of a netrin-1 polypeptide sequence as defined herein. Minor modifications thereof are included so long as they are recognizable as a sequence as defined above.

The invention also provides nucleic acids encoding the subject netrin-1 polypeptides, which nucleic acids may be part of netrin-expression vectors and may be incorporated into recombinant cells for expression and screening, transgenic animals for functional studies (e.g. the efficacy of candidate drugs for neural disease), etc. and nucleic acid hybridization probes and replication/amplification primers having a disclosed netrin cDNA specific sequence. The subject nucleic acids are isolated, meaning they comprise a sequence joined to a nucleotide other than that which it is joined to on a natural chromosome, and usually constitute at least about 0.5%, preferably at least about 2%, and more preferably at least about 5% by weight of total nucleic acid present in a given fraction. A pure nucleic acid constitutes at least about 50%, preferably at least about 90%, and more preferably at least about 95% by weight of total nucleic acid present in a given faction. The subject nucleic acids find a wide variety of applications including use as translatable transcripts, hybridization probes, PCR primers, therapeutic nucleic acids, etc.; use in detecting the presence of netrin-1 gene transcripts, e.g. allele-specific oligonucleotide (ASO) probes use to identify wild-type and mutant netrin-1 alleles in clinical and laboratory samples, in detecting or amplifying nucleic acids encoding netrin-1, and in gene therapy applications, e.g. oligonucleotides capable of modulating APP signaling and inhibiting Aβ peptide formation.

The invention also provides efficient methods of identifying pharmacological agents or lead compounds for agents capable of mimicking or modulating netrin-1 polypeptide function. A wide variety of screens may be used; for example, cell-based assays may be used for monitoring netrin-1 function and in vitro binding assays may be used to identify and monitor netrin-1 specific binding. Preferred methods are amenable to automated, cost-effective high throughput screening of natural and synthetic chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

The disclosed netrin-1 polypeptides may be used to modulate APP signaling and inhibit Aβ peptide production in situ or in vivo. For in vivo applications, the compositions are added to a retained physiological fluid such as blood or synovial fluid. For CNS administration, a variety of techniques are available for promoting transfer of the therapeutic across the blood brain barrier including disruption by surgery or injection, drugs which transiently open adhesion contact between CNS vasculature endothelial cells, and compounds which facilitate translocation through such cells. Netrin-1 polypeptides also can be administered by direct injection or infusion, topical, intratrachealinasal administration e.g. through aerosol, intraocularly, or within/on implants e.g. fibers e.g. collagen, osmotic pumps, grafts comprising appropriately transformed cells, etc. A particular method of administration involves coating, embedding or derivatizing fibers, such as collagen fibers, protein polymers, etc. with therapeutic proteins. Other useful approaches are described in Otto et al., *J Neuroscience Research* 22:83-91 (1989) and Otto and Unsicker *J Neuroscience* 10:1912-1921 (1990).

As used herein, the term "effective amount" when used in reference to administration of a netrin-1 polypeptide is intended to mean an amount of such a molecule required to effect a beneficial change in a clinical symptom, physiological state or biochemical activity targeted by a netrin-1 polypeptide of the invention. For example, an effective is an amount sufficient to decrease the extent, amount or rate of progression of plaque formation associated with Aβ peptide accumulation. The dosage of a netrin-1 polypeptide required to be therapeutically effective will depend, for example, on the severity of the symptoms to be treated, the route and form of administration, the potency and bio-active half-life of the molecule being administered, the weight and condition of the individual, and previous or concurrent therapies.

The appropriate amount considered to be an effective dose for a particular application of the method can be determined by those skilled in the art, using the teachings and guidance provided herein. For example, the amount can be extrapolated from in vitro or in vivo assays or results from clinical trials employing related or different therapeutic molecules or treatment regimes. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such a substance in depot or long-lasting form as discussed herein. A therapeutically effective amount is typically an amount of a substance that, when administered in a physiologically acceptable composition, is sufficient to achieve a plasma concentration of from about 0.1 µg/ml to about 100 µg/ml, preferably from about 1.0 µg/ml to about 50 µg/ml, more preferably at least about 2 µg/ml and usually 5 to 10 µg/ml. Therapeutic antibodies can be administered in proportionately appropriate amounts in accordance with known practices in this art. Other additives may be included, such as stabilizers, bactericides, etc. will be present in conventional amounts. Those skilled in the art will recognize that the condition of the patient can be monitored, for example, throughout the course of therapy and that the amount of the netrin-1 polypeptide that is administered can be adjusted accordingly.

The substances useful for practicing the methods of the invention can be formulated and administered by those skilled in the art in a manner and in an amount appropriate for the condition to be treated; the rate or amount of inflammation; the weight, gender, age and health of the individual; the biochemical nature, bioactivity, bioavailability and side effects of the particular compound; and in a manner compatible with concurrent treatment regimens. An appropriate amount and formulation for decreasing the severity of a neurodegenerative condition associated with beta amyloid peptide production and amyloid plaque formation in humans can be extrapolated from credible animal models known in the art of the particular disorder. It is understood, that the dosage of a therapeutic substance has to be adjusted based on the binding affinity of the substance, such that a lower dose of a substance exhibiting significantly higher binding affinity can be administered compared to the dosage necessary for a substance with lower binding affinity.

The total amount of a substance can be administered as a single dose or by infusion over a relatively short period of time, or can be administered in multiple doses administered over a more prolonged period of time. Such considerations will depend on a variety of case-specific factors such as, for example, whether the disease category is characterized by acute episodes or gradual or chronic deterioration. For a individual affected with chronic deterioration, for example, as associated with neuroinflammatory disorder such as MS, the substance can be administered in a slow-release matrice, which can be implanted for systemic delivery or at the site of the target tissue. Contemplated matrices useful for controlled release of therapeutic compounds are well known in the art, and include materials such as DepoFoam™, biopolymers, micropumps, and the like.

The netrin-1 polypeptides and functional fragments of the invention can be administered to the individual by any number of routes known in the art including, for example, systemically, such as intravenously or intraarterially. A therapeutic substance can be provided in the form of isolated and substantially purified polypeptides and polypeptide fragments in pharmaceutically acceptable formulations using formulation methods known to those of ordinary skill in the art. These formulations can be administered by standard routes, including for example, topical, transdermal, intraperitoneal, intracranial, intracerebroventricular, intracerebral, intravaginal, intrauterine, oral, rectal or parenteral (e.g., intravenous, intraspinal, intrathecal, subcutaneous or intramuscular) routes. In addition, therapeutic purified polypeptides and polypeptide fragments administered in the methods of the invention can be incorporated into biodegradable polymers allowing for sustained release useful for reducing the severity of a chronic neurodegenerative condition characterized by beta amyloid peptide production and amyloid plaque formation. Biodegradable polymers and their use are described, for example, in Brem et al., *J. Neurosurg.* 74:441-446 (1991), which is incorporated herein by reference.

A netrin-1 polypeptides and functional fragments of the invention also can be administered as a solution or suspension together with a pharmaceutically acceptable medium. Such a pharmaceutically acceptable medium can include, for example, sterile aqueous solvents such as sodium phosphate buffer, phosphate buffered saline, normal saline or Ringer's solution or other physiologically buffered saline, or other solvent or vehicle such as a glycol, glycerol, an oil or an injectable organic ester. A pharmaceutically acceptable medium can additionally contain physiologically acceptable compounds that act, for example, stabilize the neutralizing agent, increase its solubility, or increase its absorption. Such physiologically acceptable compounds include, for example, carbohydrates such as glucose, sucrose or dextrans; antioxidants such as ascorbic acid or glutathione; receptor mediated permeabilizers, which can be used to increase permeability of the blood-brain barrier; chelating agents such as EDTA, which disrupts microbial membranes; divalent metal ions such as calcium or magnesium; low molecular weight proteins; lipids or liposomes; or other stabilizers or excipients. Those skilled in the art understand that the choice of a pharmaceutically acceptable carrier depends on the route of administration of the netrin-1 polypeptide or functional fragment of the invention and on its particular physical and chemical characteristics.

Formulations suitable for parenteral administration include aqueous and non-aqueous sterile injection solutions such as the pharmaceutically acceptable mediums described above. The solutions can additionally contain, for example, buffers, bacteriostats and solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

In view of the fact that beta-amyloid plaques form in the Central Nervous System (CNS), it is understood that formulations capable of crossing the blood-brain barrier are particularly preferred embodiments for administration of a netrin-1 polypeptide and functional fragments of the invention. In a preferred embodiment, the blood-brain barrier is temporarily disrupted and a netrin-1 polypeptide is administered during simultaneously or relatively simultaneously with the disruption.

To facilitate crossing the blood-brain barrier, formulations that increase the lipophilicity of the compound are particularly desirable. For example, the neutralizing agent can be incorporated into liposomes (Gregoriadis, *Liposome Technology, Vols. I to III,* 2nd ed. (CRC Press, Boca Raton Fla. (1993)). Liposomes, which consist of phospholipids or other lipids, are nontoxic, physiologically acceptable and metabolizable carriers that are relatively simple to make and administer.

A therapeutic substance administered in the methods of the invention can also be prepared as nanoparticles. Adsorbing peptide compounds onto the surface of nanoparticles has proven effective in delivering peptide drugs to the CNS (see Kreuter et al., *Brain Research* 674:171-174 (1995)). Exemplary nanoparticles are colloidal polymer particles of polybutylcyanoacrylate with a therapeutic substance to be administered in the methods of the invention adsorbed onto the surface and then coated with polysorbate 80.

Image-guided ultrasound delivery of netrin-1 polypeptides and functional fragments of the invention through the blood-brain barrier to selected locations in the brain can be utilized as described in U.S. Pat. No. 5,752,515. Briefly, to deliver a therapeutic substance past the blood-brain barrier a selected location in the brain is targeted and ultrasound used to induce a change detectable by imaging in the central nervous system (CNS) tissues and/or fluids at that location. At least a portion of the brain in the vicinity of the selected location is imaged, for example, via magnetic resonance imaging (MRI), to confirm the location of the change. An therapeutic substance administered in the methods of the invention into the patient's bloodstream can be delivered to the confirmed location by applying ultrasound to effect opening of the blood-brain barrier at that location and, thereby, to induce uptake of the substance.

In addition, polypeptides called receptor mediated permeabilizers (RMP) can be used to increase the permeability of the blood-brain barrier to molecules such as therapeutic or diagnostic substances as described in U.S. Pat. Nos. 5,268, 164; 5,506,206; and 5,686,416. These receptor mediated permeabilizers can be intravenously co-administered to a host with molecules whose desired destination is the cerebrospinal fluid compartment of the brain, for example, in the treatment of a neurodegenerative condition. The permeabilizer polypeptides or conformational analogues thereof allow therapeutic substances to penetrate the blood-brain barrier and arrive at their target destination.

In embodiments where the netrin-1 polypeptide is conjugated to a second polypeptide, the second peptide or protein can be therapeutic or can be a peptide capable of absorptive-mediated or receptor-mediated transcytosis through the subject's blood brain barrier. In another embodiment, the netrin-1 polypeptide is administered through an artificial LDL particle comprising an outer phospholipid monolayer and a solid lipid core, wherein the outer phospholipid monolayer comprises at least one apolipoprotein and the solid lipid core contains the netrin-1 polypeptide. In a further embodiment, the netrin-1 polypeptide is bound to a nanoparticle comprising a hydrophilic protein to which apolipoprotein E is coupled or bound, or co-administered with an antiglucocorticoid drug in a sufficient amount to increase permeability of the subject's blood brain barrier.

In other embodiments, the netrin-1 polypeptide is chemically modified for enhanced transmembrane transport, for example, by covalent linking of a fatty acid to the netrin-1 polypeptide or glycosylation of said netrin-1 polypeptide.

In current treatment regimes for Alzheimer's Disease, more than one compound is often administered to an individual for management of the same or different aspects of the disease. Similarly, a therapeutic substance can advantageously be formulated with a second therapeutic compound such as an anti-inflammatory compound, immunosuppressive compound or any other compound that manages the same or different aspects of the disease. Such compounds include, for example, cholinesterase inhibitors such as Razadyne® (formerly known as Reminyl®) (galantamine), Exelon® (rivastigmine), Aricept® (donepezil), and Cognex® (tacrine), N-methyl D-aspartate (NMDA) antagonists such as Namenda® (memantine); and those medicines that are administered to control behavioral symptoms of AD such as sleeplessness, agitation, wandering, anxiety, and depression. Additional medicines can be coadministered with a netrin-1 polypeptide or functional fragment thereof, treat mild cognitive impairment (MCI) associated with early stages of Alzheimer's Disease, for example, donepezil (Aricept). The skilled practitioner will be able to select further candidates for coadministration with a polypeptide of the invention from the numerous medicines and compounds known in the art as useful in the clinical management of AD and its symptoms including, for example, vitamins E and C; nonsteroidal anti-inflammatory drugs (NSAIDs); antioxidants, *Ginkgo biloba* and estrogen. Contemplated methods of the invention include administering a therapeutic substance useful in the methods of the invention alone, in combination with, or in sequence with, such other compounds. Alternatively, combination therapies can consist of fusion proteins, where the therapeutic netrin-1 polypeptide of the invention is linked to a heterologous protein. In embodiments where the netrin-1 polypeptide is conjugated to a second polypeptide, the second peptide or protein can be therapeutic or can be a peptide capable of absorptive-mediated or receptor-mediated transcytosis through the subject's blood brain barrier.

A netrin-1 polypeptide of the invention or functional fragment thereof, which effectively reduces or inhibits Aβ peptide production or amyloid plaque formation can also be used to enhance memory function, especially the elderly. A subject can be administered such agents and assayed for improved memory capability. A netrin-1 polypeptide of the invention or functional fragment thereof can be administered by known methods such as those described above.

In a further embodiment, the invention provides methods to diagnose, stage or prognose the presence or development of Alzheimer's disease based on the brain concentration ratio of Aβ peptides to netrin-1. The invention thus provides methods useful in choosing a therapy for an individual afflicted with a Alzheimer's disease, including methods for diagnosis, methods of predicting an increased risk of developing Alzheimer's disease, methods of choosing a therapy for an individual, methods of predicting or monitoring response to a therapy for an individual, methods of determining the efficacy of a therapy in an individual, and methods of determining the prognosis for an individual. The methods are based on determining the brain concentration ratio of Aβ peptides to netrin-1 and comparing this ratio to a standard. A higher ratio of Aβ peptides to netrin-1 would be expected with decreased suppression of Aβ peptide production by netrin-1.

Unless defined otherwise, the scientific and technological terms and nomenclature used herein have the same meaning as commonly understood by a person of ordinary skill in the art to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, New York).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. It is understood that modifications which do not substantially affect the activity of the various embodiments of this invention are also included within the definition of the invention provided herein. Accordingly, the following examples are intended to illustrate but not limit the present invention.

Example I

Netrin-1 Functions as a Ligand of APP

This example demonstrates that chemotropic and survival molecule, netrin-1 functions as a ligand of the orphan receptor, APP, and interacts directly with Aβ peptide.

Cells, Transfection Procedures, and Purified and Recombinant Proteins:

Transient transfections of HEK293T (human embryonic kidney) or B103 (neuroblastoma) cells were performed using the lipofectamine reagent (Invitrogen). Primary cortical neurons were obtained from E16.5 embryos and cultured for 3 days in Neurobasal media supplemented with B27 (Invitrogen, Carlsbad, Calif.). Recombinant netrin-1 (Apotech Corp.) was added 24 h after plating and every 24 h. C-myc tagged Netrin-1 was purified from netrin-1-producing 293-EBNA cells, according to Serafini et al., Cell 78:409-424 (1994). GST-netrin-1 was produced as previously described Tanikawa et al., Nat. Cell. Biol. 5:216-223 (2003). bFGF was from ABcam. Recombinant APPs, Aβ1-42 (and Aβ1-17) and DCC-EC-Fc were purchased from Sigma Aldrich, Anaspec, and R&D Systems, respectively. Recombinant APLP2 ectodomain was obtained via Flagagarose affinity purification using the supernatant of HEK293 cells stably expressing ecto-APLP2-Flag.

Plasmid Constructs:

Full-length APP695 (pcDNA3-APP), netrin-1 (pGNET1-myc), netrin-2 (pGNET2-myc), netrin G1 (pcDNA4-G1-netrin), domains V and VI of netrin-1 (pCEP4-netV-VI), APPC100 (pcINeo-C100), APLP1 (pcINeo-APLP1), APLP2 (pcDNA3-APLP2) and Disabled1 (pcDNA3-DAB1) expressing constructs were described previously (Lu et al., Nat. Med. 6:397-404 (2000), Lu et al., Ann. Neurol. 54:781-789 (2003), Galvan et al., J. Neurochem. 82:283-294 (2002), Serafini et al., Cell 78:409-424 (1994), Keino-Masu et al., Cell 87:175-185 (1996) and Homayouni et al., J. Neurosci. 19:7507-7515 (1999)). APP613-695 was obtained by PCR using pcINeo-C100 as a PCR template and the following primers: 5'-CACCATGTTGGTGTTCTTTGCAGA-3' (SEQ ID NO:3) and 5'-CTAGTTCTGCATCTGCTCAAA-3' (SEQ ID NO:4) and inserted into a pcDNA3.1TOPOd (Invitrogen). PG5E1B-luc (Gal4 reported construct), pMst (Gal), pMst-APP (APP-Gal4), pMst-APP* (mutated form of APP unable to bind to Fe65) were previously described Cao and Sudhof, Science 293:115-120 (2001). TrkC (pCDNA3-TrkC-HA) was obtained by inserting into pCDNA3 vector the rat TrkC coding sequence obtained from a pCMX-Trkc plasmid kindly provided by S. Meakey. APLP2 ectodomain expressing construct used for stable transfection of HEK293 cells was obtained by addition of a stop codon via a QuikChange® (Stratagene) procedure using pcDNA-APLP2 as a template and the following primers: 5'-GAGGACTTCAGTCTGTAGAGTAGCAGTGCTCTC-3' (SEQ ID NO:5) and 5'GAGAGCACTGCTACTCTACAGACTGAAGTCCTC-3' (SEQ ID NO:6).

ELISA binding assay 96-wells plates (Immunoplate Maxisorp, Nunc) were coated overnight at room temperature with a secreted form of APP (respectively APLP2, Aβ, Aβ1-17) at a concentration of 2.5 μg/ml (respectively: 2.5, 0.18, 0.07 μg/ml). After 1 hour blocking at 37° C. with 5% FCS in PBS, wells were washed (0.05% Tween20 in PBS), followed by netrin-1 (Human Net 1-FlagM2, Apotech) or bFGF incubation in a concentration range from 0.225 nM-60 nM at 37° C. for 1 hour (0.05% FCS in PBS). After being washed four times, wells were incubated with an anti-FlagM2 (Sigma-Aldrich) or anti-bFGF antibody in blocking buffer for 30 minutes at 37° C., followed by another wash step. An anti-mouse antibody coupled to HRP (Jackson ImmunoResearch, Inc) was added at a concentration of 0.8 μg/ml for 1 hour at 37° C. Colorimetric intensity was measured at a wavelength of 490 nm using a Victor station (Wallac).

Western Blot and Immunoprecipitation:

Western blots were performed as described Mehlen et al., Nature 395:801-804 (1998), using APP (C-terminal epitope: Sigma-Aldrich; N-terminal epitope: Sigma-Aldrich), Aβ (biosource), DAB-1 (Exalpha Biologicals), Fe65 (Upstate), Flag M2 (Sigma-Aldrich), GST (Sigma-Aldrich), c-myc (Sigma-Aldrich), P75-NGFR (abcam), TrkC (Santa-Cruz) or Net-1 anti-mouse monoclonal (R&D Systems) antibody. Co-immunoprecipitations from HEK293 and B103 were performed as previously described Forcet et al., Proc. Natl. Acad. Sci. USA 98:3416-3421 (2001). Co-immunoprecipitations from primary culture were performed using the microbeads system developed by Miltenyi Biotech.

Commissural and Cortical Axon Outgrowth:

Dorsal spinal cord explants from E13 rat embryos were cultured as previously described Serafini et al., Cell 78:409-424 (1994), Forcet et al., Nature 417:443-447 (2002) and Corset et al., Nature 407:747-750 (2000). To study cortical axon outgrowth, APP mutant mice were used. APP mutant mice were in a mixed background of C57BL6, 129SvEv and 129 Ola and were described before Heber et al., J. Neurosci. 20:7951-7963 (2000). E13.5 mice embryos originating from the same cross APP+/−xAPP+/−were further dissected while genotyping was performed a posteriori. The brain was excised from the skull, and the pial membranes were removed. Small pieces (approx. 400 μm×700 μm) of cortical tissue, that spanned the full thickness of the cortical wall, were dissected from the caudal half of the each cortical hemisphere as shown in FIG. 5a. Explants were transferred into collagen. After polymerization, gels were covered with F12-DMEM supplemented with 10% inactivated horse serum (Invitrogen), and penicillin/streptomycin and were incubated at 37° C. in a 5% CO2 atmosphere during 20 hours in the presence or absence of netrin-1. Both commissural and cortical axons were stained with an anti-β-tubulin antibody (Babco). Quantification of axonal length was done as previously described Corset et al., Nature 407:747-750 (2000).

Briefly, the total length of axon bundles was measured for each explant and normalized to the values obtained from explants cultured with purified netrin-1. In the case of cortical axons and because some cortical axon outgrowth was detected in the absence of netrin-1, this basal growth was withdrawn from each condition before normalization.

Confocal Analysis on Primary Cultures of Neurons:

Primary cultures of neurons were fixed in 4% PFA and stained with various primary antibodies (5A3/1 G7, anti-netrin 64, or antiserum I (R1155)) followed by Alexa568- and/or Alexa488-conjugated anti-mouse and/or anti-rabbit secondary antibodies respectively. Stacks of images (z step=0.25 mm) were acquired with a laser scanning confocal microscope (Nikon PCM-2000) using a 100× objective and a 2.7 digital zoom, collected using SimplePCI software (Compix Inc., Lake Oswego, Oreg.) and processed in an SGI Octane R12 computer running Bitplane's Advanced Imaging Software suite.

Organotypic Culture and Aβ Release Determination:

PDAPP(J20) mice were described before Galvan et al., Proc. Natl. Acad. Sci. USA 103:7130-71354 (2006). 250 μm coronal brain slices were cut from P1 transgenic and non-transgenic littermates' whole brains to establish organotypic cultures. Tissues were incubated in 0.5% D-glucose, 25% fetal bovine serum, 25% Hank's buffered saline solution, in Opti-MEM (Invitrogen). Recombinant netrin-1, NGF or IGF-1 was added to the media immediately after plating and every 24 h. After 3 days, Aβ1-40 and Aβ1-42 were quantitated in the culture media using specific ELISA assays (Biosource, Camarillo, Calif.). To measure Aβ in a context of lower netrin-1 concentration, transgenic PDAPP(J20) mice were crossed with netrin-1+/−mice. Netrin-1 mutant mice were described before Serafini et al, Cell 87:1001-1014 (1996) and Forcet et al., Nature 417:443-447 (2002). Mice with adequate genotypes (PDAPP-netrin-1+/− and PDAPP-netrin-1+/+) were analyzed for Aβ level using the specific above ELISA assay.

Figure 1B:
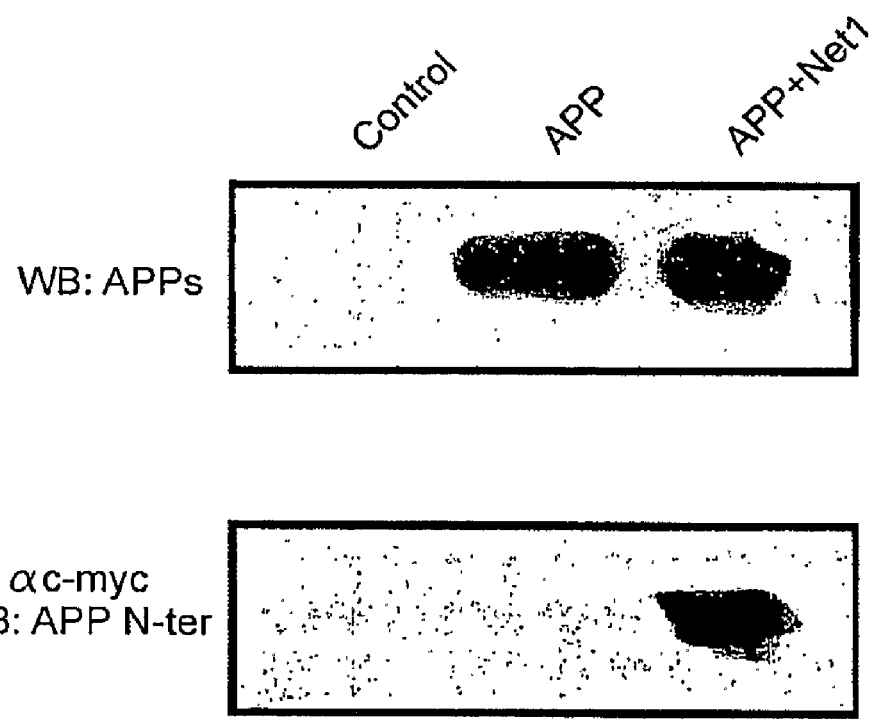
Figure 1C:
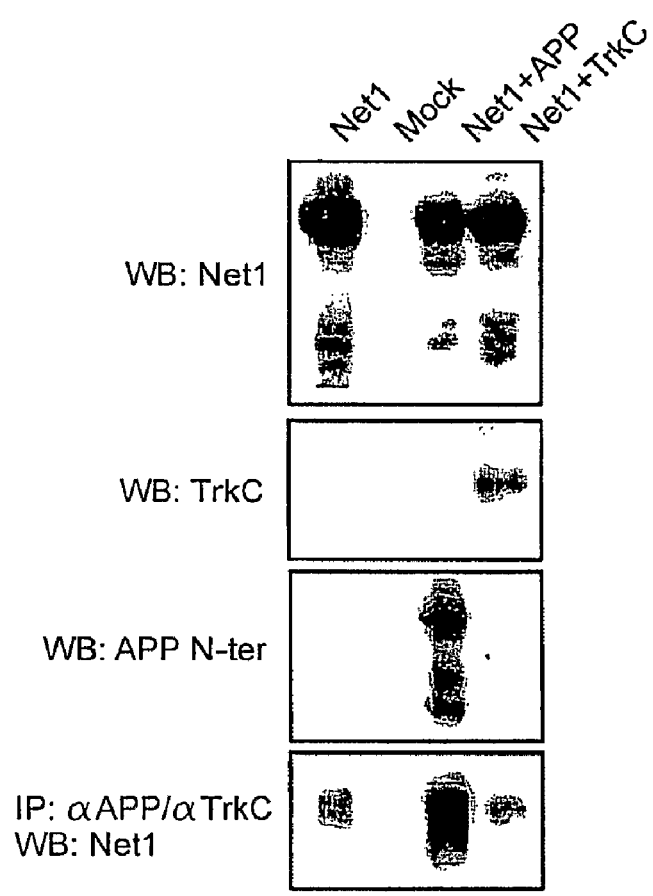

APP and netrin-1 were therefore co-expressed in HEK293T cells and, as shown in FIGS. 1A and B, APP co-immunoprecipitated with netrin-1. Briefly, HEK293T cells were transiently transfected with myc-tagged netrin-1 and/or APP and/or TrkC. Either conditioned medium (Panel 1b) or cell lysate (Panels 1a and 1c) was utilized for immunoprecipitation, using either an anti-c-myc antibody (for netrin) (Panels 1a and 1b), an anti-N-terminal APP antibody (Panel 1c) or an anti-TrkC antibody (Panel 1c). Immunoprecipitations were subjected to polyacrylamide gel electrophoresis, transferred, and probed with antibodies raised against N-terminal APP (Panels 1a and 1b) or netrin-1 (Panel 1c). The co-immunoprecipitation between APP and netrin-1 also occurred in the reverse direction when APP instead of netrin-1 was pulled-down (FIG. 1c). As a negative control, another transmembrane receptor, TrkC, failed to coimmunoprecipitate with netrin-1 (FIG. 1c).

Figure 1D:
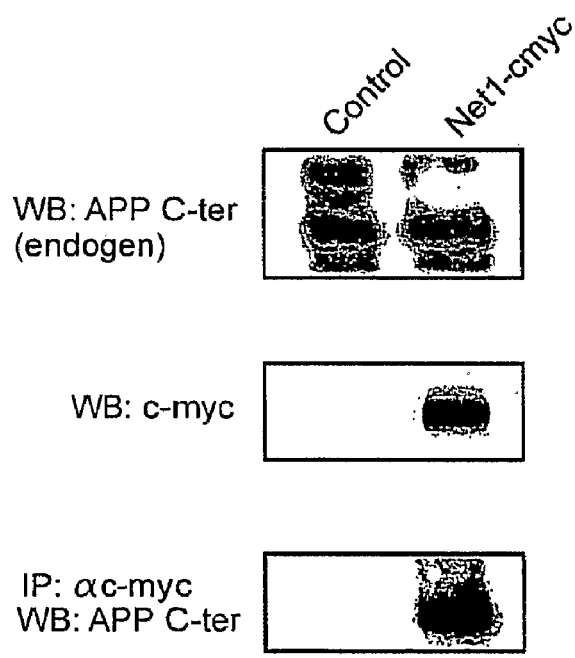
Figure 1E:
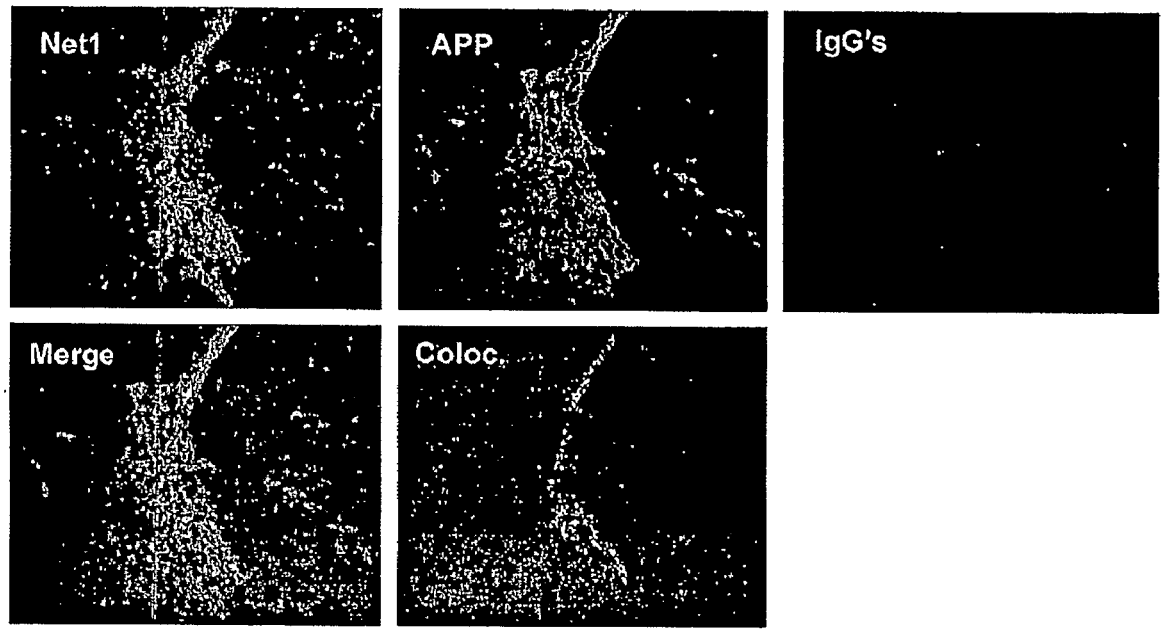
Figure 1F:
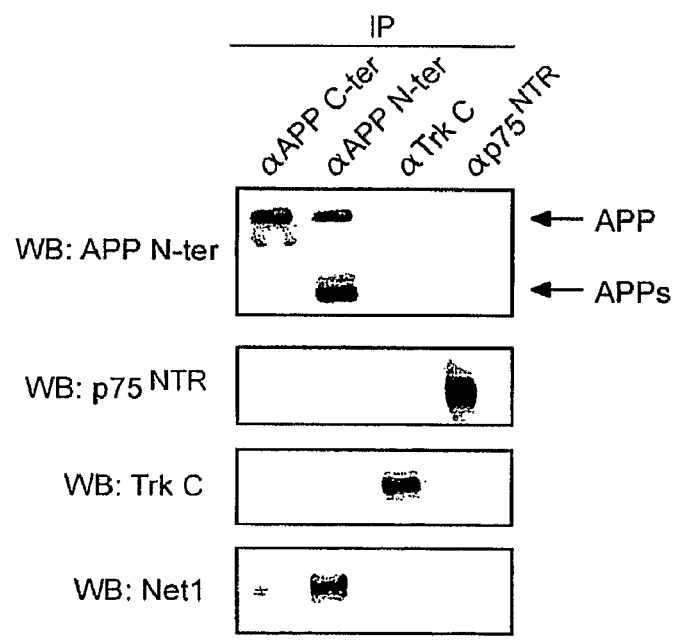

HEK293T cells were transfected with netrin-1 expressing construct or not and endogenous APP was, after c-myc (netrin-1) pull-down, revealed using an anti-C-terminal APP antibody (FIG. 1D). Not only ectopically expressed APP (FIG. 1a-c) but also endogenous APP could be immunoprecipitated with netrin-1 in HEK293T (FIG. 1D). Because these immunoprecipitations were performed in cells in which APP and netrin-1 are expressed in a non-physiological setting, the putative APP/netrin-1 interaction in primary cortical neurons from E16.5 mouse embryos was investigated by first analyzing whether endogenous APP is co-localized with endogenously expressed netrin-1 by confocal microscopy. FIG. 1E shows colocalization of 5A3/1G7 (APP extracellular domain) with netrin-1 in growth cones of primary cortical neurons.

Briefly, primary cultures of neurons from DBA/2J embryos were fixed in 4% PFA and stained with 5A3/1G7 and anti-netrin 64 or with mouse and rabbit IgGs followed by Alexa568- and Alexa488-conjugated anti-mouse and anti-rabbit secondary antibodies respectively. Stacks of images (z step=0.25 mm) were acquired with a laser scanning confocal microscope (Nikon PCM-2000) using a 100× objective and a 2.7 digital zoom, collected using SimplePCI software (Compix Inc., Lake Oswego, Oreg.) and processed in an SGI Octane R12 computer running Bitplane's Advanced Imaging Software suite. Analysis of colocalization was done using the Coloc algorithm in Imaris Bitplane. The Pearson correlation coefficient of channel A (green) and channel B (red) inside the colocalized region (c) was used as a measure of the degree of colocalization 36. Panels shown: Net1 (netrin-1); APP; merge; Coloc (colocalization channel); IgG's (mouse and rabbit IgGs).

Figure 1G:
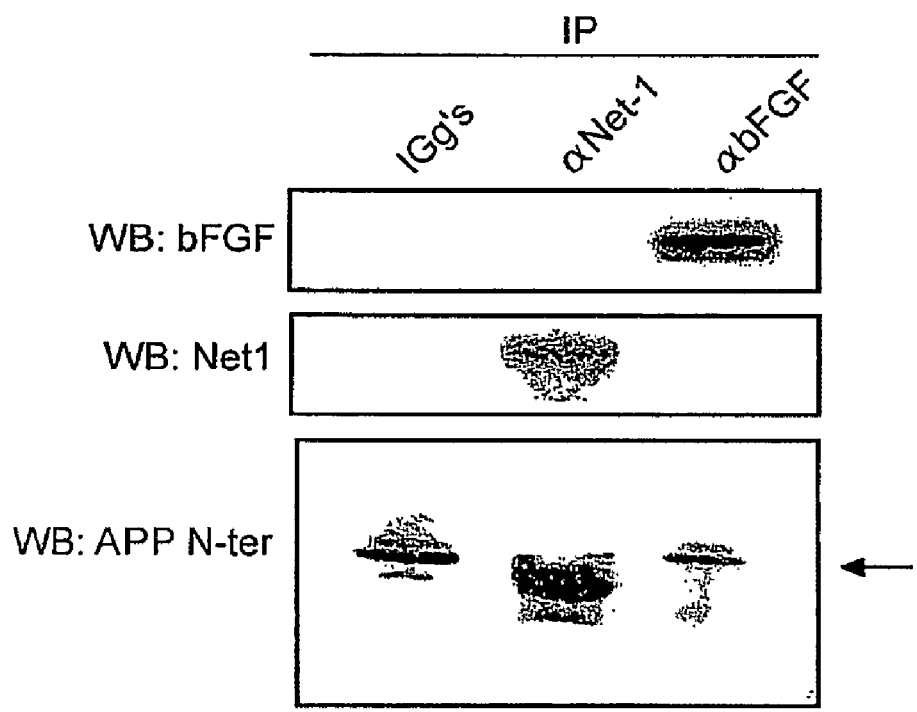
Figure 1H:
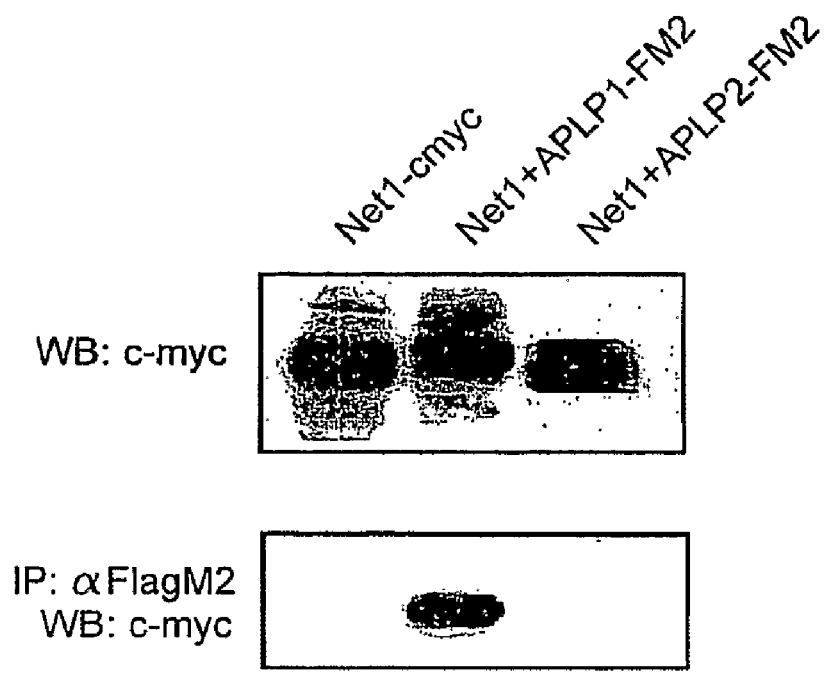

To obtain the results shown in Figures F and G, cortex from E16.5 mouse embryos were collected and semi-dissociated and cells lysates were submitted to immunoprecipitation using anti-APP (C-terminal or N-terminal), anti-TrkC or anti-p75NTR antibody (FIG. 1F) or anti-netrin-1 (anti-mouse netrin-1: anti-mNet1), anti-bFGF antibody or respective irrelevant IgGs (FIG. 1G) for the pull-down. Immunoblot were then performed using either APP, p75 ntr or TrkC antibody (FIG. 1F) or netrin-1 or bFGF antibody (FIG. 1G). HEK293T cells were transiently transfected with myc-tagged netrin-1, netrin-2 or ΔC netrin-1 (net (V,VI)), netrin G0, and APP, Flag-tagged APLP1 or APLP2 (FIGS. 1 H through I). Cell lysate was utilized for immunoprecipitation, using either an anti-c-myc antibody (for netrin) (FIG. 1I) or FlagM2 antibody (for APLP1 and APLP2) (FIG. 1H).

In FIG. 1, panels a through d, h and i, the upper panels show expression of the proteins prior to pull-down, and the lower panel(s) is (are) after pull-down. In panels 1f and g, all panels show expression of the proteins after pull-down (panel 1j) 150 ng of recombinant αAPPs was added to increasing concentrations of purified c-myc-tagged netrin-1 in 1 ml reaction buffer. Netrin-1 pull-down was performed (with anti-c-myc), and the concentration of αAPPs pulled down with netrin-1 was quantified after Western blotting, using anti-APP antibody and NIH image software. A similar analysis was performed with DCC-EC. Bottom panels: input of αAPPs and DCC-EC shown by Western blot.

An Elisa assay was developed as described above to determine the KdAPP/netrin. 2.5 µg/ml of αAPPs protein was coated in 96-wells plate and various netrin-1 concentrations were added. Similar experiment was performed using the pair APP/bFGF or the pair APLP2/netrin-1. Quantification of the interaction is indicated in panel 1k by the measurement of the optic density (intensity). Kd determination was derived from a simulated Scatchard plot (Bound/Estimated Free=f (Bound)).

As shown in FIG. 1E, APP co-localizes with netrin-1, especially in growth cones. Co-immunoprecipitation of endogenous proteins using either anti-netrin-1 or anti-APP antibody for the pull-down shows that netrin-1 interacts with APP in the developing cortex, whereas in the same setting, netrin-1 fails to interact with p75$^{ntr}$ or TrkC (FIG. 1F), and APP fails to interact with bFGF (FIG. 1G), a molecule that shares many characteristics of netrin-1. Thus, endogenous netrin-1 specifically interacts with endogenous APP in the developing brain.

Figure 1I:
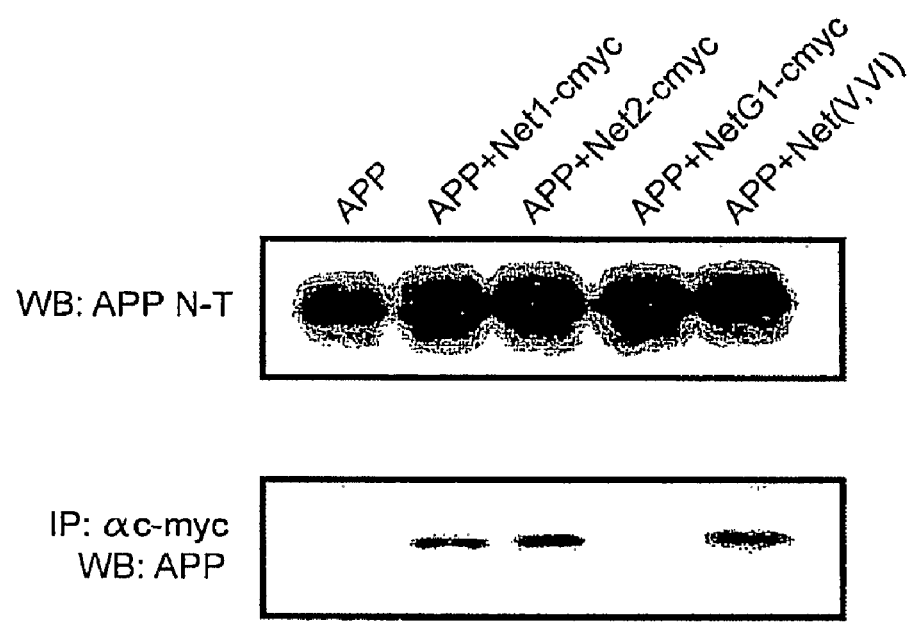

To further analyze whether netrin-1 interaction is restricted to APP, coimmunoprecipitation studies were also performed in HEK293T cells using epitope-tagged APLP1 and APLP2, and whereas netrin-1 was found to immunoprecipitate with the former, no such interaction was observed with the latter (FIG. 1h). Furthermore, in addition to netrin-1, netrin-2 was also found to interact with APP, whereas no interaction was detected between APP and the more divergent netrin molecule, netrin G1 (FIG. 1I).

Because both netrins and APP are heparin-binding proteins, it was assessed whether a netrin-1 mutant deleted for Domain C (which contains the major heparin-binding domain, but is dispensable for netrin-1 function retains the ability to interact with APP. As shown in FIG. 1I, this mutant netrin-1 does indeed retain the ability to interact with APP.

Figure 1J:
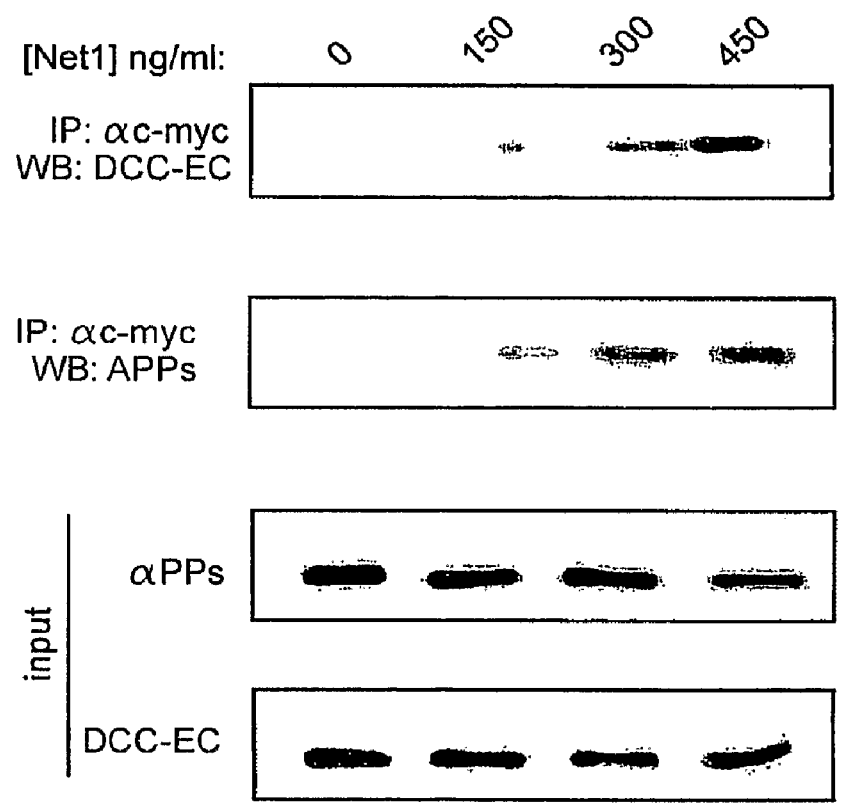
Figure 1K:
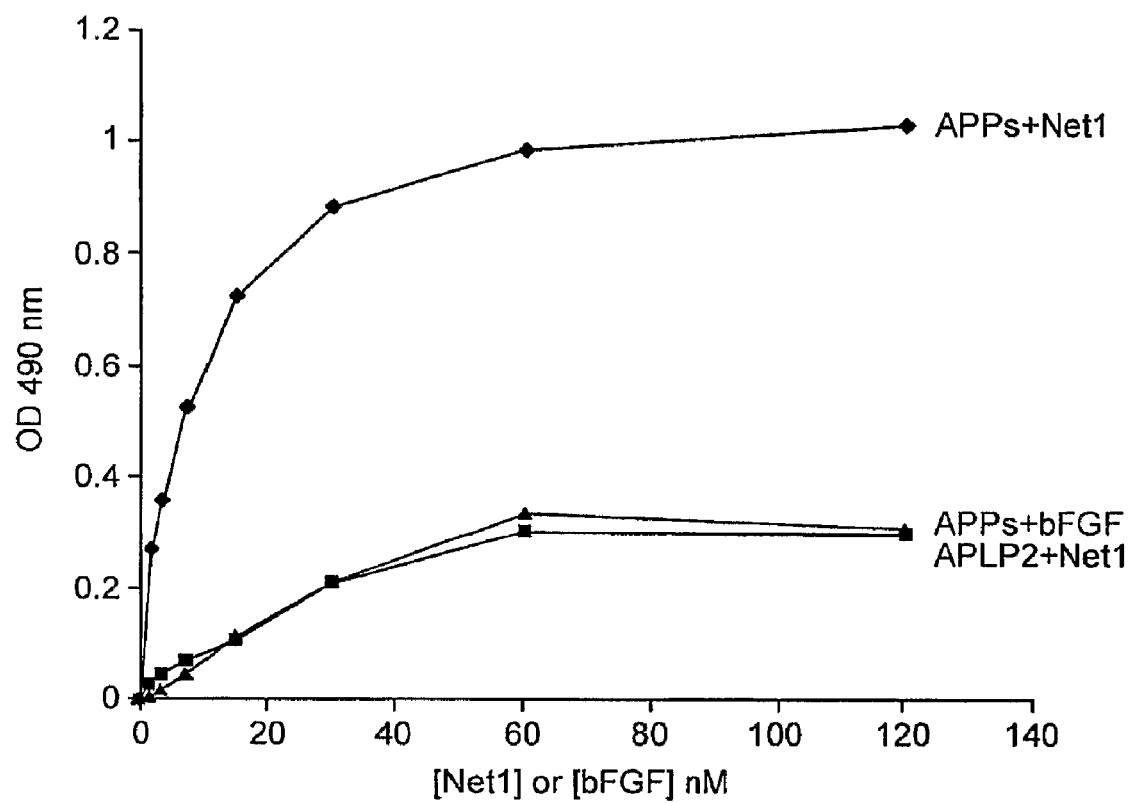

To exclude the possibility of an indirect interaction between netrin-1 and APP, direct in vitro interaction was assessed by immunoprecipitation and ELISA assays on recombinant αAPPs, DCC or APLP2 ecto-domain, with recombinant netrin-1 or bFGF. As shown in FIGS. 1J-K, immunoblots and ELISA assays revealed a specific interaction of APP with netrin-1 while bFGF/APP and netrin-1/APLP2 failed to show specific binding. The affinity of netrin-1 for APPs is the same order of magnitude as its affinity for DCC (estimated KdAPP/netrin of 6 nM, compared to the known KdDCC/netrin-1 of 10 nM 10). Taken together, these data support the notion that netrin-1 interacts with APP with an affinity that is similar to that of its previously described physiological interaction with DCC.

Figure 2A:
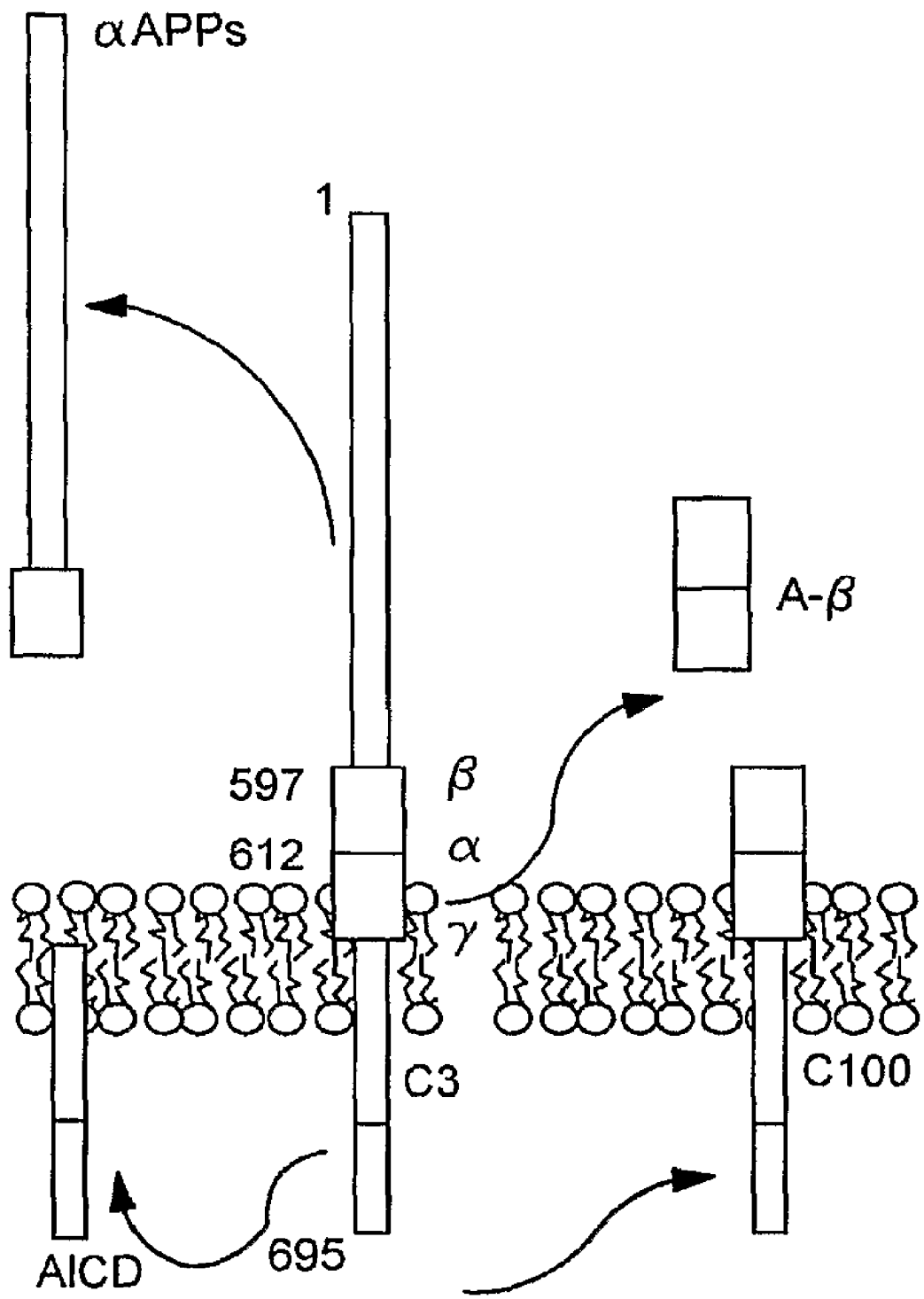
FIG. 2. A netrin-1 binding domain of APP lies within the Aβ region of APP. a, Schematic representation of APP. b, HEK293T cells were co-transfected with a C100 (APP597-695) or APP613-695-expressing construct in the presence or in the absence of a netrin-1 expression construct. Immunoprecipitation was performed using anti-c-myc (for netrin-1) for the pull-down and an antibody raised against the C-terminal domain of APP for the immunoblot. c, Same as FIG. 1j, but in the presence (or absence) of a large excess of Aβ (150 ng). Note that αAPPs failed to be pulled-down with netrin-1 in the presence of Aβ.
Figure 2B:
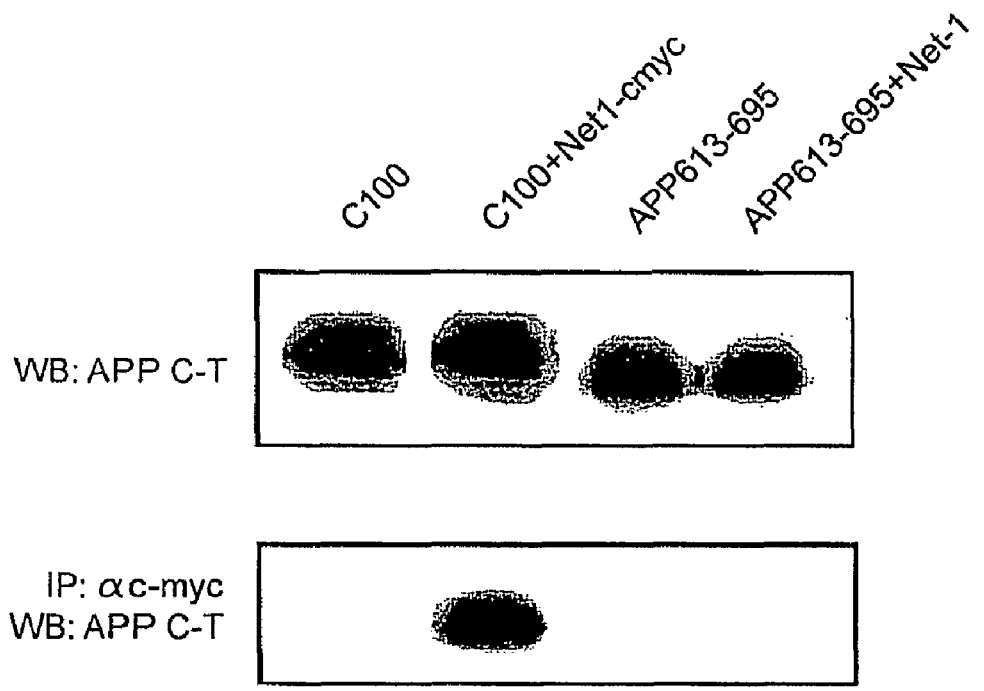
Figure 2C:
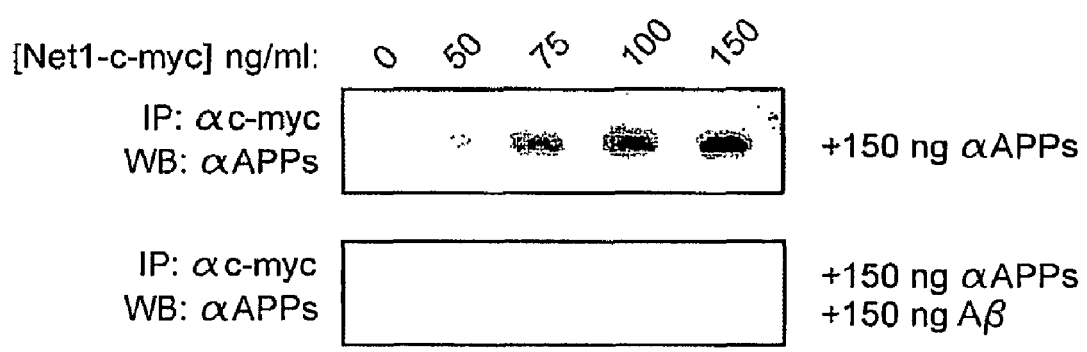

To define the APP domain required for the APP-netrin-1 interaction, the carboxy-terminal C100 protein, derived from the β-secretase cleavage of APP (see FIG. 2A), was pulled down with netrin-1 (FIG. 2B). Taken together with the finding that, in vitro, the αAPPs protein interacts with netrin-1 (FIGS. 1 J and K), these observations suggested that a binding region of APP is localized between the β-cleavage site and the α-cleavage site. In agreement with this hypothesis, deletion of the region from the α-cleavage site to the β-cleavage destroyed the putative interaction of C100 with netrin-1 (FIG. 2b). Thus, netrin-1 interacts with a region included within the Aβ domain of APP. To provide further proof for this conclusion, the in vitro pull-down of αAPPs with netrin-1 was performed in the presence of an excess of Aβ. As shown in FIG. 2c, the presence of Aβ completely inhibited the αAPPs pull-down with netrin-1.

FIG. 2a shows a schematic representation of APP. HEK293T cells were co-transfected with a C100 (APP597-695) or APP613-695-expressing construct in the presence or in the absence of a netrin-1 expression construct. Immunoprecipitation was performed using anti-c-myc (for netrin-1) for the pull-down and an antibody raised against the C-terminal domain of APP for the immunoblot (FIG. 2b). FIG. 2c parallels FIG. 1j, but in the presence (or absence) of a large excess of Aβ (150 ng). Significantly, αAPPs failed to be pulled-down with netrin-1 in the presence of Aβ.

Figure 3A:
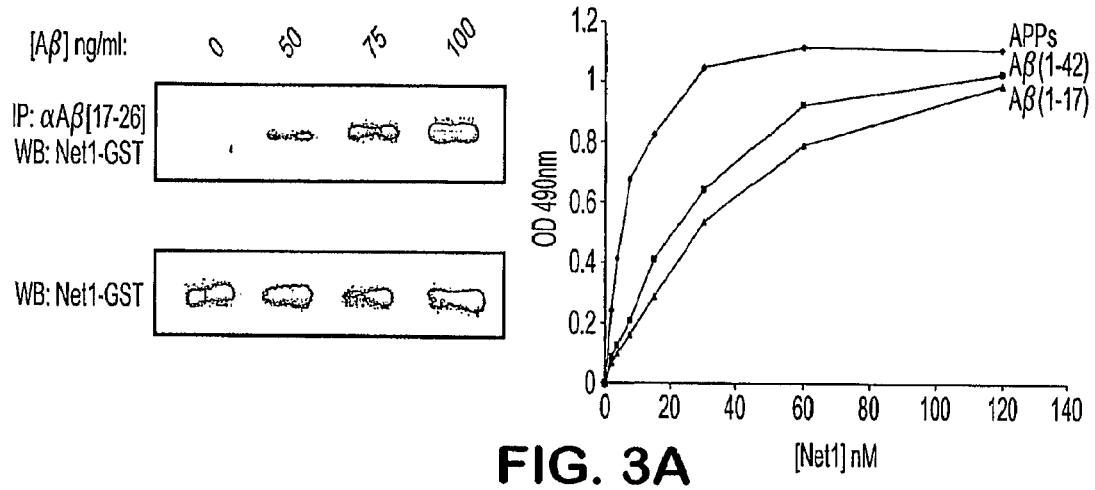
FIG. 3. Aβ interacts with netrin-1 and inhibits netrin-1 function. a, Netrin-1 immunoprecipitates with Aβ. 150 ng of Aβ were incubated with increasing concentrations of GST-netrin-1 in 1 ml of reaction buffer. Pull-down was performed using anti-Aβ specific antibody, and netrin-1 was detected by Western blot using anti-GST antibody. An Elisa assay was performed as in FIG. 1k. 0.18 µg/ml of Aβ or 0.07 µg/ml of Aµ1-17 protein was coated in 96-wells plate and various netrin-1 concentrations were added. Quantification of the interaction is indicated here by the measurement of the optic density (intensity). b, E13 dorsal spinal cord explants were cultured for 18 hours or 40 hours (40 hrs) in collagen gel, either without a netrin-1 source (−), or with purified netrin-1 (Net-p). Explants were either left untreated (−), treated with 15 µg/ml of Aβ or of Aβ1-17. A quantification is shown. The total number of explants that were quantified from 4 distinct experiments varied from 24-36 per tested condition. Values shown are means±SEM. Scale bars: 200 µm.

The above described results show that APP interacts with netrin-1, and that a region of APP that corresponds to the amino-terminal portion of the Aβpeptide is sufficient for this interaction. To confirm that the Aβ peptide itself is sufficient for interaction with netrin-1, and to test this possibility, netrin-1 co-immunoprecipitation with Aβ was analyzed. As shown in FIG. 3A, recombinant netrin-1 interacts in a concentration-dependent manner with the Aβ peptide. Interestingly, not only Aβ but also a smaller fragment of Aβ, Aβ 1-17—i.e., the 17 first amino acids of Aβ (a less toxic peptide than full-length Aβ)—interacted with netrin-1, albeit with a reduced affinity ($Kd_{A\beta/netrin-1}$:22 nM, $Kd_{A\beta1-17/netrin-1}$:30 nM). Because Aβand Aβ1-17 were found to interact with netrin-1, it was next analyzed whether Aβ or Aβ1-17 may interfere with netrin-1 function. Netrin-1 has been identified as a molecule that promotes commissural axon outgrowth. Dorsal spinal cord explants from E13 rat embryos were grown for 16-18 h in collagen gels, with or without purified netrin-117. As previously shown 8,17, the presence of netrin-1 promoted axon outgrowth (FIG. 3b).

Figure 3B:
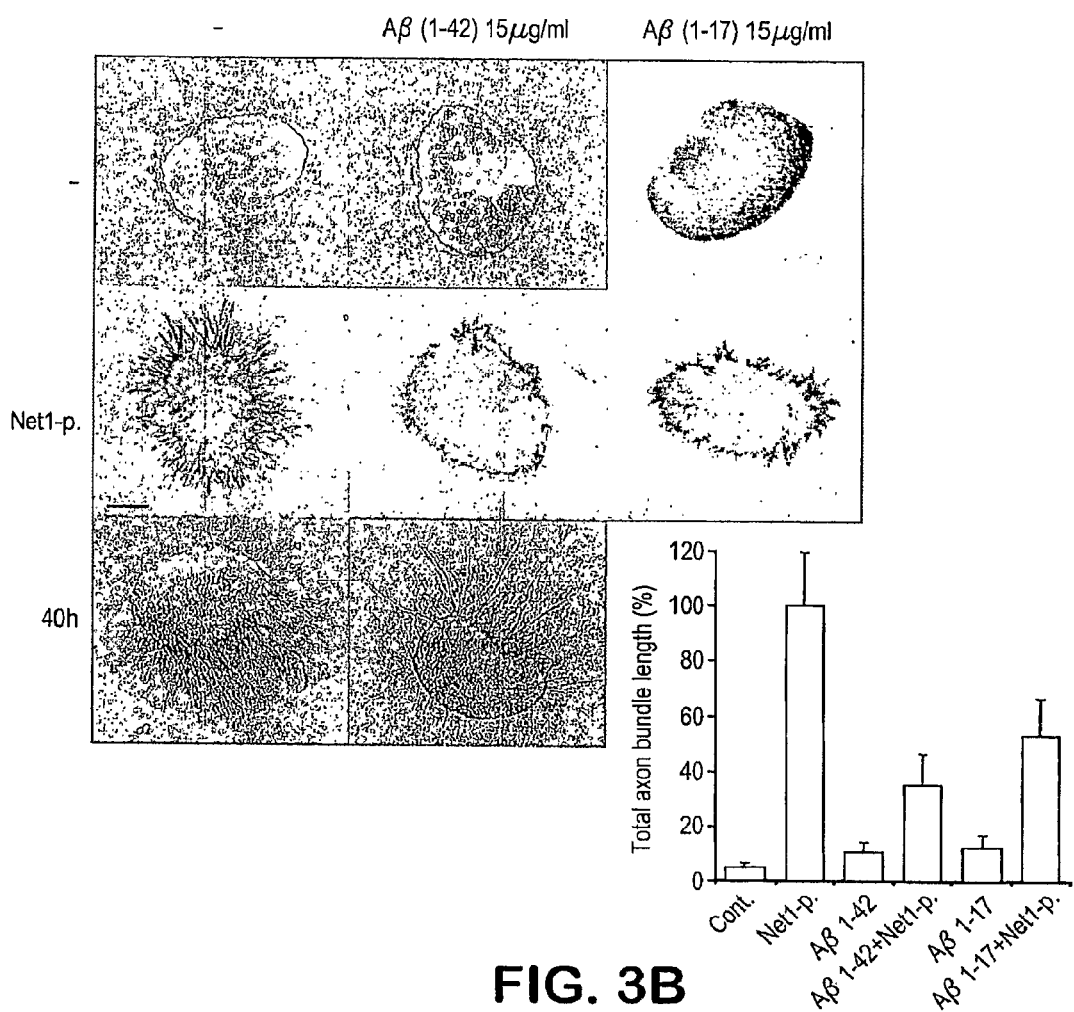

However, the addition of Aβ or of Aβ1-17, highly reduced netrin-1-induced axon extension (p<0.0001) (FIG. 3). Similar results were obtained when the source of netrin-1 was provided by explants from floor plate, the natural source of netrin-1 (not shown). This effect did not simply represent a general inhibition of axon outgrowth (e.g., due to Aβ toxicity), but was specific for netrin-1 signaling, since netrin-independent commissural axon outgrowth (which is observed when spinal cord explants are grown for 40 h) 8 18 was unaffected by Aβ (FIG. 3b, total axon length per explant (mean±SEM), without Aβ: 607±126 µm (n=12), with Aβ: 657±127 µm (n=8)). Thus, netrin-1 may interact not only with APP but also with Aβ, and soluble Aβ may consequently affect netrin-1 function.

150 ng of Aβ were incubated with increasing concentrations of GST-netrin-1 in 1 ml of reaction buffer, Pull-down was performed using anti-Aβ specific antibody, and netrin-1 was detected by Western blot using anti-GST antibody. An Elisa assay was performed described above and shown in FIG. 1K. 0.18 µg/ml of Aβ or 0.07 µg/ml of Aβ1-17 protein was coated in 96-wells plate and various netrin-1 concentrations were added (FIG. 3A). Quantification of the interaction is indicated in FIG. 3 by the measurement of the optic density (intensity). To obtain the results shown in FIG. 3b, E13 dorsal spinal cord explants were cultured for 18 hours or 40 hours (40 hrs) in collagen gel, either without a netrin-1 source (−), or with purified netrin-1 (Net-p). Explants were either left untreated (−), treated with 15μ/ml of Aβ or of Aβ1-17. A quantification is shown. The total number of explants that were quantified from 4 distinct experiments varied from 24-36 per tested condition. Values shown are means±SEM. Scale bars: 200 μm.

Example II

Netrin-1 Mediates APP Signaling

This example shows that netrin-1 modulates APP signaling and suppresses net production of Aβ peptide.

Figure 4A:
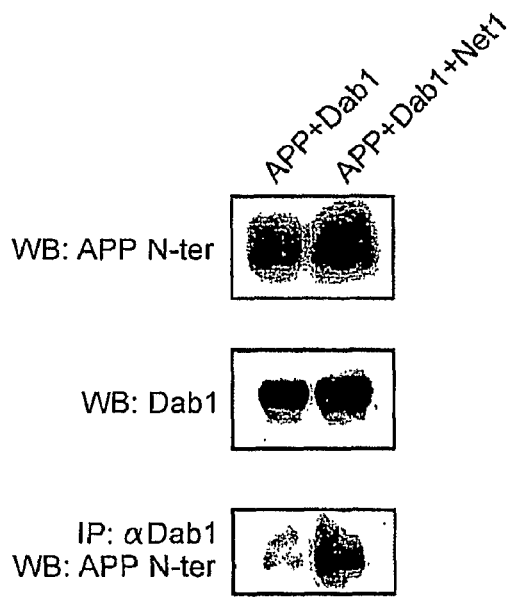
FIG. 4. Netrin-1 signals through APP. a, HEK293T cells were transiently co-transfected with APP and DAB-1-expressing constructs, and further incubated in the presence (or absence) of netrin-1. Pull-down was performed using an anti-DAB-1 antibody, and APP was detected in this pull-down using an N-terminal anti-APP antibody. b, B103 cells were transiently transfected with APP and further incubated with (or without) netrin-1. Endogenous Fe65 was immunoprecipitated using anti-Fe65 antibody, and N-terminal anti-APP antibody was used to detect APP within the pull-down. In a-b, the upper panels represent APP and DAB-1 (or Fe65) before the pull-down, the lower panel being APP detected in the immunoprecipitation. c, HEK293T cells were co-transfected with APP-Gal4 or APP*-Gal4 together with a Gal4-luciferase reporter (pG5E1B-luc) construct in a 1:1 ratio. 300 ng/ml of Netrin-1 (or of bFGF) was added to the culture after 24 hours and 48 hours after transfection, cells were collected and cell lysate were assessed for luciferase activity using the Promega's luminescence measurement assay and a Victor biostation (Perkin-Almer). An histogram plot is presented. Standard deviations are indicated (n=5). d, Primary neuronal cultures from E16.5 hAPP transgenic embryos (PDAPP(J20) in C57BL/6J background) were treated with vehicle (PBS) or with 300 ng/ml netrin-1 added to the culture media every 24 h for 3 days, starting 1.5 day after plating. Cultures were fixed, treated with RNAse and stained with a 1:1000 dilution of an antibody specific for the C-terminal domain of APP (amino acids 649-664, antiserum I (R1155)[37]) followed by Alexa488-conjugated donkey anti-rabbit IgG (Invitrogen) and counterstained with TOTO-3 to visualize DNA. Stacks of images (z step=250 nm) were acquired with a laser scanning confocal microscope (Nikon PCM-2000) at 600× magnification and collected with SimplePCI (Compix Inc., Sewickley, Pa.) software. For each condition, five separate fields were chosen in which individual cells were clearly distinguishable (avoiding clumps of neuronal bodies). A representative maximum intensity projection image of fields acquired for each condition is shown. e, Distribution of intensity of anti-I immunoreactivity across nuclei (Upper panel, green traces overlaid on images) representative of each condition were determined using the Histogram module of the Zeiss 510 LSM image analysis software. Lower panel, plots of intensity as a function of distance. f and g, Individual volumes (9×9×6 µm) of single nuclei (control, n=53; netrin-1, n=51) were cropped from stacks of confocal images and analyzed separately using the Imaris Isosurface algorithm (Imaris Bitplane, Zurich, Switzerland). f, Maximum-intensity projections of stacks of control and netrin-1-treated neuronal nuclei. Representative images are shown. g, Numbers of anti-I immunoreactive voxels in neuronal nuclei. A significant increase of APP C-terminal immunoreactive voxels was observed in nuclei of neurons had been treated with netrin-1 (p<0.05, unpaired Student's t test).

HEK293T cells were transiently co-transfected with APP and DAB-1-expressing constructs, and further incubated in the presence (or absence) of netrin-1. Pull-down was performed using an anti-DAB-1 antibody, and APP was detected in this pull-down using an N-terminal anti-APP antibody (FIG. 4A).

Figure 4B:
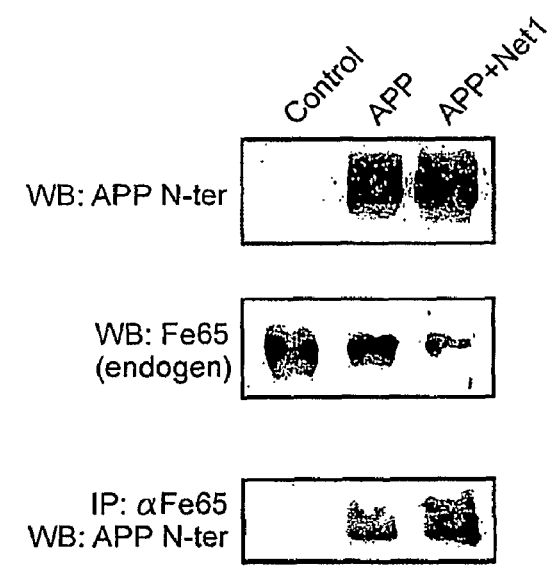

B103 cells were transiently transfected with APP and further incubated with (or without) netrin-1. Endogenous Fe65 was immunoprecipitated using anti-Fe65 antibody, and N-terminal anti-APP antibody was used to detect APP within the pull-down (FIG. 4B). In FIGS. 4A and B, the upper panels represent APP and DAB-1 (or Fe65) before the pull-down, the lower panel being APP detected in the immunoprecipitation.

HEK293T cells were co-transfected with APP-Gal4 or APP*-Gal4 together with a Gal4-luciferase reporter (pG5E1B-luc) construct in a 1:1 ratio. 300 ng/ml of Netrin-1 (or of bFGF) was added to the culture after 24 hours and 48 hours after transfection, cells were collected and cell lysate were assessed for luciferase activity using the Promega's luminescence measurement assay and a Victor biostation (Perkin-Elmer). A histogram plot is presented. Standard deviations are indicated (n=5).

Figure 4C:
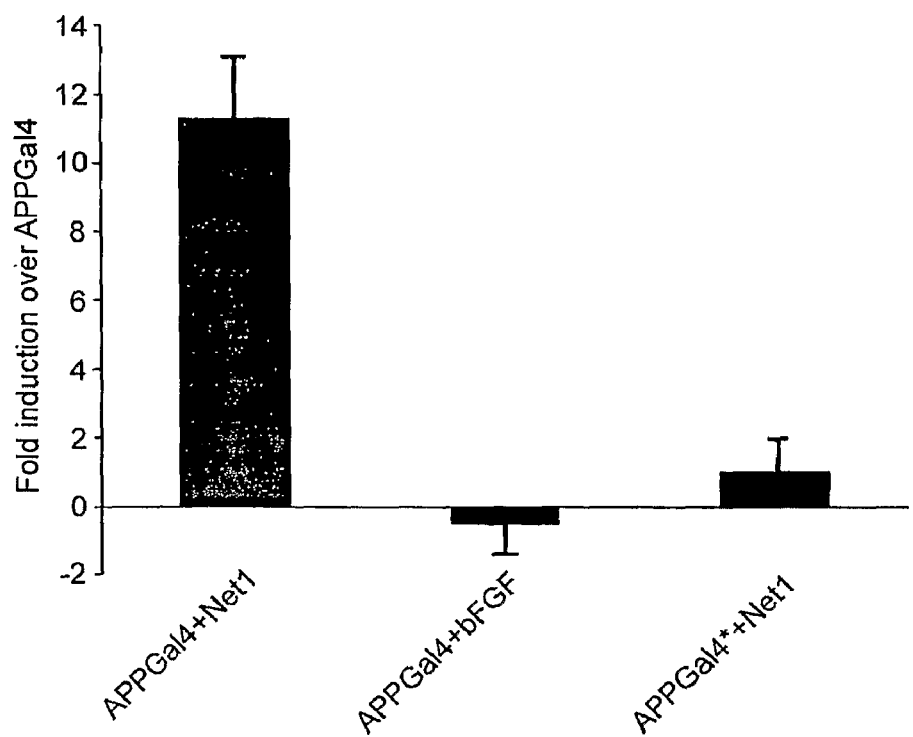
Figure 4D:
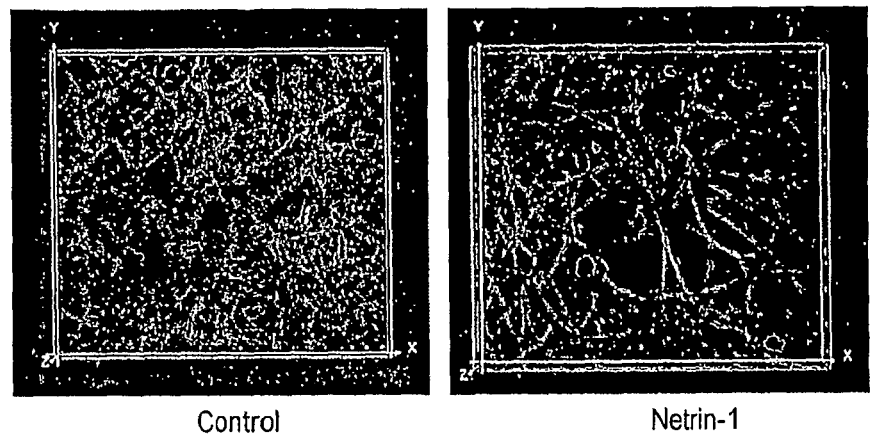
Figure 4E:
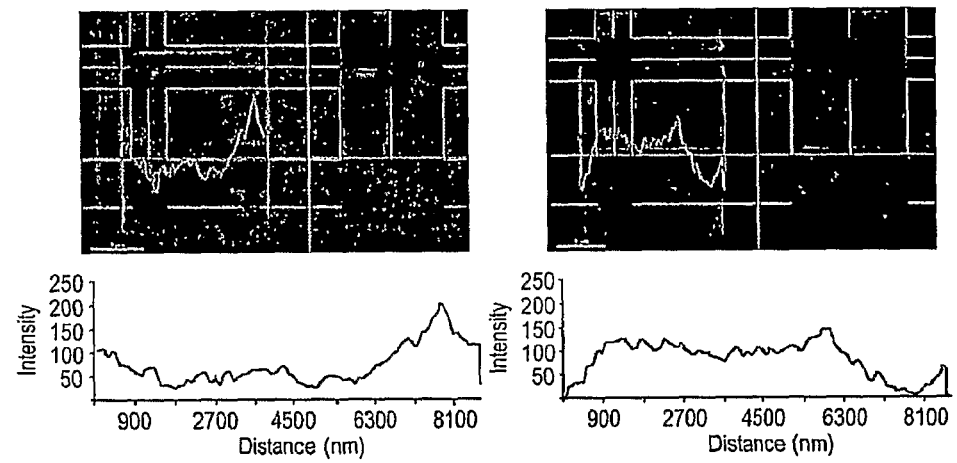

For the results shown in FIG. 4D, primary neuronal cultures from E16.5 hAPP transgenic embryos (PDAPP(J20) in C57BL/6J background) were treated with vehicle (PBS) or with 300 ng/ml netrin-1 added to the culture media every 24 h for 3 days, starting 1.5 day after plating. Cultures were fixed, treated with RNAse and stained with a 1:1000 dilution of an antibody specific for the C-terminal domain of APP (amino acids 649-664, antiserum I (R1155) 37) followed by Alexa488-conjugated donkey anti-rabbit IgG (Invitrogen) and counterstained with TOTO-3 to visualize DNA. Stacks of images (zstep=250 nm) were acquired with a laser scanning confocal microscope (Nikon PCM-2000) at 600× magnification and collected with SimplePCI (Compix Inc., Sewickley, Pa.) software. For each condition, five separate fields were chosen in which individual cells were clearly distinguishable (avoiding clumps of neuronal bodies). A representative maximum intensity projection image of fields acquired for each condition is shown.

The, distribution of intensity of anti-I immunoreactivity across nuclei (Upper panel, green traces overlaid on images) representative of each condition were determined using the Histogram module of the Zeiss 510 LSM image analysis software. Lower panel, plots of intensity as a function of distance.

Figure 4F:
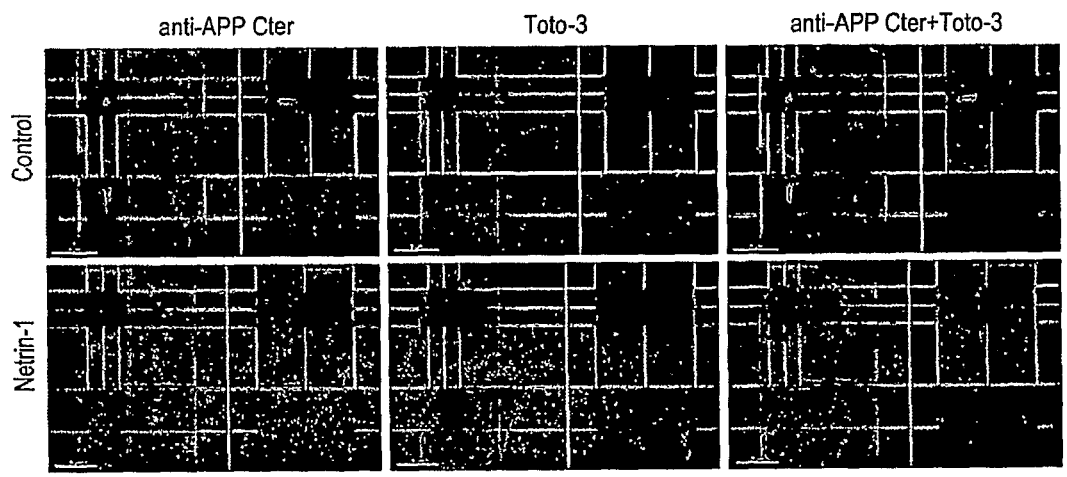
Figure 4G:
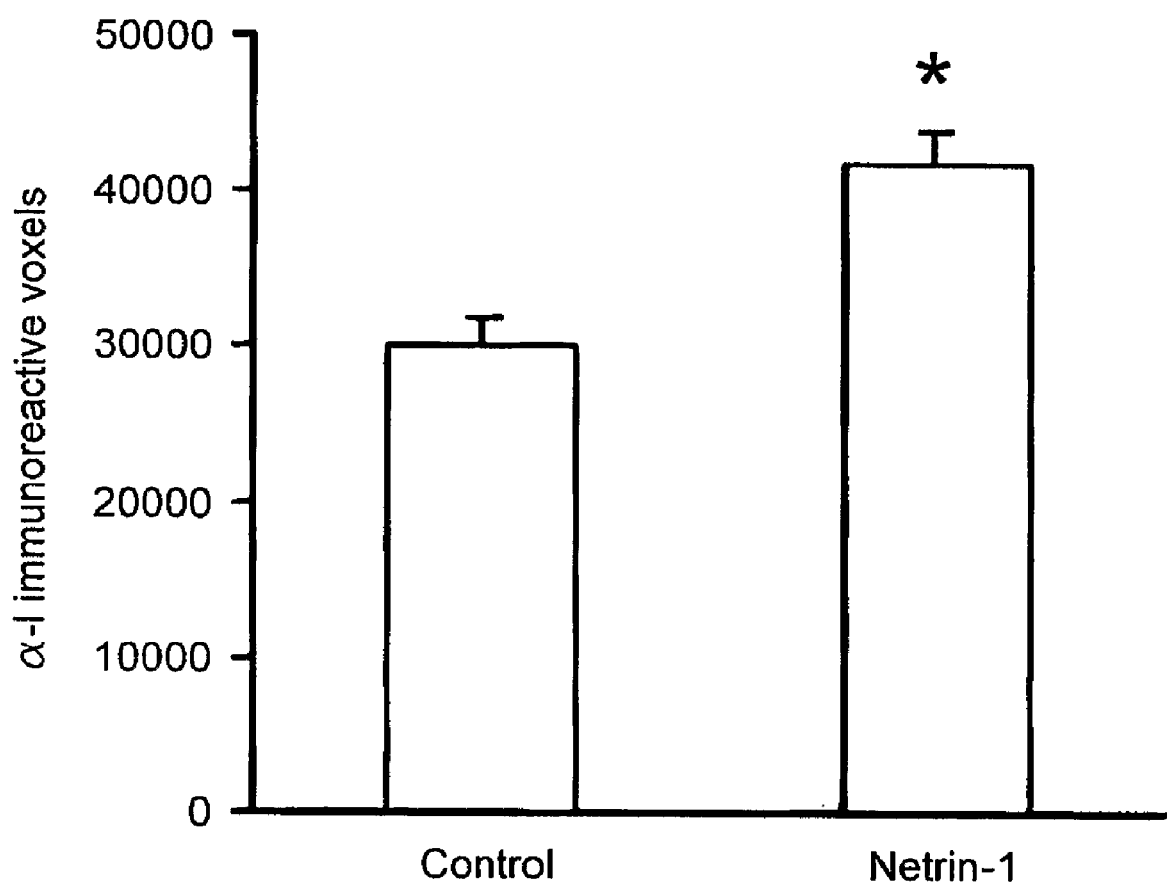

For FIGS. 4F and 4G, individual volumes (9×9×6 μm) of single nuclei (control, n=53; netrin-1, n=51) were cropped from stacks of confocal images and analyzed separately using the Imaris Isosurface algorithm (Imaris Bitplane, Zurich, Switzerland). FIG. 4F shows maximum-intensity projections of stacks of control and netrin-1-treated neuronal nuclei. Representative images are shown. FIG. 4G shows the numbers of anti-I immunoreactive voxels in neuronal nuclei. A significant increase of APP C-terminal immunoreactive voxels was observed in nuclei of neurons had been treated with netrin-1 ($p<0.05$, unpaired Student's t test).

The adaptor protein DAB-1 has been shown to interact with the intracellular domain of APP (Trommsdorff et al., *J Biol Chem* 273: 33556 (1998)). As shown in FIG. 4A, netrin-1 enhanced the recruitment of DAB-1 to APP (FIG. 4A). Similarly, the adaptor protein Fe65 has been shown to interact with the intracellular domain of APP and to provide a mechanism for the coupling of APP to the cytoskeleton (Ando et al., *J Biol Chem* 276: 40353 (2001)).

Fe65 was also shown to be responsible for APP intracellular domain (AICD)-dependent gene transcription. Indeed, it was shown that in the presence of Fe65, the intracellular domain of APP migrates to the nucleus and initiates APP-dependent transcription of a specific set of genes via the requirement of TIP60 (Cao and Sudhof, *Science* 293:115 (2001); Kimberly et al., *J Biol Chem* 276: 40288 (2001); Cao and Sudhof, *J Biol Chem* 279: 24601 (2004)). FIG. 4B shows that, in APP-transfected B103 cells, the Fe65 interaction with APP is mainly observed when netrin-1 is added. According to the model proposed, this netrin-1-dependent enhanced interaction of Fe65 with APP should lead to an increased AICD activity. To test this, the elegant transactivation assay developed previously was used in which the DNA binding domain of Gal4 is fused to APP and transactivation is monitored with a Gal4-dependent reporter plasmid.

As shown in FIG. 4c, netrin-1 triggers a robust APP-dependent gene transactivation in HEK293T, while bFGF has no effect on the Gal4-dependent reporter. This netrin-1 dependent, APP-dependent transactivation is abolished when APP is mutated at the Fe65 binding site. To further study netrin-1 effects on AICD, AICD was analyzed in primary cortical neurons derived from E16.5 embryos from PDAPP mice expressing a human APP minigene carrying the Swedish and Indiana familial Alzheimer's disease (AD) mutations 25. As AICD-nuclear localization is an important—even though dispensable—event in AICD-dependent transactivation 23, the effect of netrin-1 on the translocation of APP C-terminal-immunoreactive fragments into nuclei of hAPP transgenic cortical neurons was assessed. As shown in FIG. 4*defg*, APP C-terminal-immunoreactive fragments are significantly increased in nuclei of netrin-1-treated neurons. Taken together, these results suggest that netrin-1 is likely to exert a functional effect on APP signaling.

Example III

APP is Required for Netrin-1-Mediated Cortical Axon Outgrowth

This example demonstrates that APP is required for netrin-1 dependent cortical axon guidance during brain development.

Cortical explants were dissected out from E13.5 wild-type or APP mutant embryos as indicated in upper right panel of FIG. 5 and cultured in collagen in the presence or not of 375 ng/ml of netrin-1. FIG. 5A shows representative images of axon outgrowth in the different tested conditions. For FIG. 5B, the total number of explants that were quantified from 5 distinct experiments varied from 8-12 per tested condition. Values shown are means±SEM. Scale bars: 200 μm. A Kruskall-Wallis test was used comparing the overall condition, $p=0.001$. A Mann-Whitney test was also used to compare +/+ versus +/− ($p=0.036$), and +/− versus −/− ($p<0$-4).

To demonstrate the in vivo relevance of the described effect of netrin-1 on APP signaling further, it was investigated whether APP may explain part of the known function of netrin-1 as an axon guidance cue during nervous system development. It is noteworthy that netrin-1 mutant mice display profound defects in the developing nervous system, and that a major portion of this phenotype has been attributed to netrin's role as an axonal cue for its receptor, DCC, because DCC mutant mice exhibit similar defects in the developing nervous system. However, APP-null mice also display similar neural developmental defects, the severity of which depends on genetic background: these defects include abnormalities in the developing corpus callosum and other commissures 26. In particular, the similar defect of corpus callosum described in both APP and netrin-1 mutant mice could be the result of a defect in axon guidance of a sub-population of cortical neurons. To assess this possibility, explants from the caudal half region of the cortex of E13.5 wild-type mouse embryos were dissected out and cultured in collagen gels. While in the absence of netrin-1 only sparse outgrowth was observed, addition of netrin-1 led to a robust outgrowth (FIG. 5), confirming that cortical axons are responsive to netrin-1 27. When a similar experiment was performed with cortical explants from APP −/− mutant embryos, however, the effect of netrin-1 was markedly diminished. Thus netrin-1-induced axon outgrowth of cortical neurons is mediated at least in part by APP. Together with the colocalization of APP and netrin-1 at the level of the growth cone in primary cortical neurons, these data demonstrate that APP is part of a netrin-1 signaling receptor complex and is involved in the axon guidance activity of netrin-1 during brain development.

Example IV

Netrin-1 Binding to APP Suppresses A-Beta Peptide Formation

This example demonstrates that netrin-1 inhibits net Aβ peptide production.

Figure 6A:
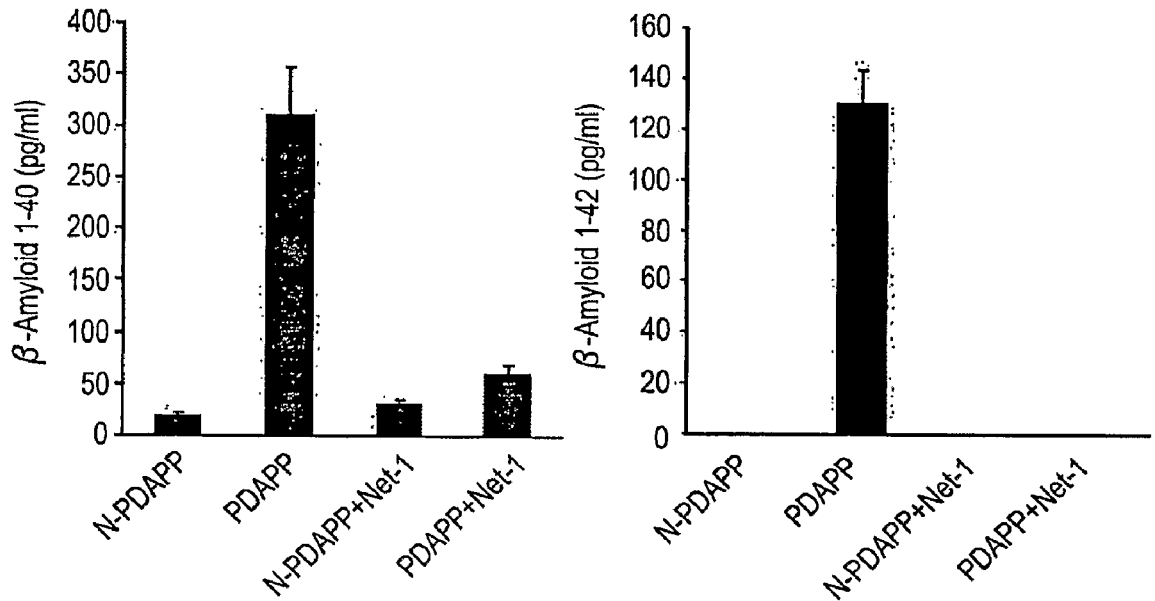
FIG. 6. Netrin-1 inhibits net Aβ peptide production. a, Brain slices from PDAPP transgenic mice and control non-transgenic littermates (NPDAPP) were cultured in the presence or absence of netrin-1 (90 ng/ml). Supernatants were harvested after 3-5 days and evaluated by ELISA assay for Aβ1-40 and Aβ1-42. 90 ng/ml of netrin-1 were added to all Aβ standards to rule out netrin-1 interference with binding of the antibodies used in the ELISA to their epitopes on Aβ. NGF (250 ng/ml) or IGF-1 (100 ng/ml) was also added as control and failed to have any effect on Aβ level (not shown). b, Netrin-1 expression (inset) and net Aβ1-40 production were measured in 5-7 month-old PDAPP/netrin-1+/− or PDAPP/netrin-1+/+ mice by ELISA. Fold increase is presented as the ratio between average Aβ levels detected in PDAPP-netrin-1+/− mice and that in PDAPP-netrin-1+/+ mice. 4 cohorts of similar age animals (netrin-1+/+ and +/−) were studied. Total number of mice studied: 16. ANOVA test: comparing +/− versus +/+ in the 4 groups (p<0.027), comparing +/− versus +/+ in the whole population (p=0.0005).
Figure 6B:
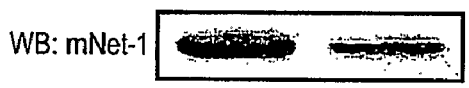
Figure 6B:
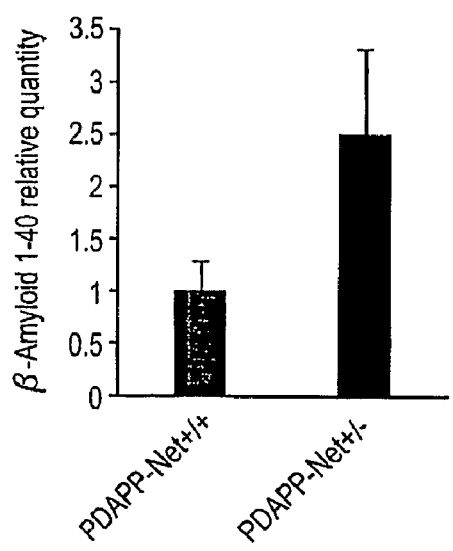

Because Alzheimer's disease pathogenesis is thought to be mediated at least in part through APP processing resulting in Aβ production, the effect of netrin-1 on Aβ peptide production in hAPP transgenic mice that model of Alzheimer's disease (von Rotz et al., *J Cell Sci* 117:4435 (2004)) was analyzed. Whole brain slice cultures from PDAPP transgenic and non-transgenic littermates were treated with vehicle or with netrin-1 and were evaluated by ELISA assay for the production of Aβ 1-40 and Aβ 1-42. As shown in FIG. 6a, the Alzheimer model transgenic mice displayed a marked increase in Aβ 1-40 and Aβ 1-42 net production over that of the control mice (non-transgenic littermates), but this was suppressed by the addition of netrin-1. In complementary in vivo studies, netrin-1 hemizygote mice (netrin nulls are non-viable) were crossed with hAPP transgenic mice, and cerebral Aβ concentrations in the progeny were quantitated by ELISA assay. The PDAPP transgenic netrin-1 hemizygotes (PDAPP-netrin-1+/−) showed a decreased netrin-1 level in the cortex compared to wild-type mice (PDAPP-netrin-1+/+) (FIG. 6b, inset). Quantitation of Aβ revealed a significant increase in Aβ levels in netrin-1 hemizygotes compared to wild-type mice (FIG. 6b, $p<0.027$), hence strengthening the view of netrin-1 as a key regulator of Aβ level.

Brain slices from PDAPP transgenic mice and control non-transgenic littermates (NPDAPP) were cultured in the presence or absence of netrin-1 (90 ng/ml). Supernatants were harvested after 3-5 days and evaluated by ELISA assay for Aβ1-40 and Aβ1-42. 90 ng/ml of netrin-1 were added to all Aβ standards to rule out netrin-1 interference with binding of the antibodies used in the ELISA to their epitopes on Aβ (FIG. 6A). NGF (250 ng/ml) or IGF-1 (100 ng/ml) was also added as control and failed to have any effect on Aβ level (not shown).

Netrin-1 expression (FIG. 6B, inset) and net Aβ 1-40 production were measured in 5-7 month-old PDAPP/netrin-1+/− or PDAPP/netrin-1+/+ mice by ELISA. FIG. 6B shows fold increase as the ratio between average Aβ levels detected in PDAPP-netrin-1+/− mice and that in PDAPP-netrin-1+/+ mice. 4 cohorts of similar age animals (netrin-1+/+ and +/−) were studied. Total number of mice studied: 16. ANOVA test: comparing +/− versus +/+ in the 4 groups ($p<0.027$), comparing +/− versus +/+ in the whole population ($p=0.0005$).

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

We claim:

1. A method for reducing or inhibiting net beta-amyloid peptide production comprising administering to a subject in need thereof an effective amount of a composition comprising:
   1) a polypeptide comprising SEQ ID NO:1,
   2) a polypeptide comprising SEQ ID NO:1 lacking Domain C,
   3) a polypeptide comprising domains V and VI of SEQ ID NO: 1,
   4) a polypeptide comprising SEQ ID NO: 1 lacking a signal sequence, or
   5) the expression product of SEQ ID NO: 2,
   that a) binds to a naturally occurring APP protein and b) inhibits Aβ peptide production, wherein the composition is an amount effective to inhibit Aβ peptide production and wherein the composition is in a form for delivery across the blood brain barrier or is administered by direct injection into the central nervous system.

2. The method of claim 1, wherein the composition mimics netrin-1-mediated signal transduction by altering the localization, protein-protein binding and/or enzymatic activity of an intracellular protein involved in an APP signal pathway.

3. The method of claim 1, further comprising administering an artificial LDL particle comprising an outer phospholipid monolayer and a solid lipid core, wherein the outer phospholipid monolayer comprises at least one apolipoprotein and the solid lipid core contains the composition.

4. The method of claim 1, wherein said polypeptide is bound to a nanoparticle comprising a hydrophilic protein to which apolipoprotein E is coupled or bound.

5. The method of claim 1, wherein said composition is co-administered with an antiglucocorticoid drug in a sufficient amount to increase permeability of the subject's blood brain barrier.

6. The method of claim 1, wherein the polypeptide is conjugated to a second polypeptide, wherein the second polypeptide is capable of absorptive-mediated or receptor-mediated transcytosis through the subject's blood brain barrier.

7. The method of claim 1, wherein said polypeptide is chemically modified for enhanced transmembrane transport.

8. The method of claim 7, wherein said polypeptide is (a) covalently linked to a fatty acid or (b)glycosylated.

9. A method for reducing or inhibiting amyloid plaque formation comprising administering to a subject in need thereof an effective amount of a composition comprising:
   1) a polypeptide comprising SEQ ID NO:1,
   2) a polypeptide comprising SEQ ID NO:1 lacking Domain C,
   3) a polypeptide comprising domains V and VI of SEQ ID NO: 1,
   4) a polypeptide comprising SEQ ID NO: 1 lacking a signal sequence, or
   5) the expression product of SEQ ID NO: 2,
   that a) binds to a naturally occurring APP protein and b) inhibits Aβ peptide production, wherein the composition is an amount effective to inhibit Aβ peptide production and wherein the composition is in a form for delivery across the blood brain barrier or is administered by direct injection into the central nervous system.

10. The method of claim 1, wherein the polypeptide comprises SEQ ID NO: 1 lacking domain C.

11. The method of claim 1, wherein the polypeptide comprises domains V and VI of SEQ ID NO: 1.

12. The method of claim 1, wherein the polypeptide comprises SEQ ID NO: 1 lacking a signal sequence.

13. The method of claim 1, wherein the composition comprises the expression product of SEQ ID NO: 2.

14. The method of claim 9, wherein the polypeptide comprises SEQ ID NO: 1 lacking domain C.

15. The method of claim 9, wherein the polypeptide comprises domains V and VI of SEQ ID NO: 1.

16. The method of claim 9, wherein the polypeptide comprises SEQ ID NO: 1 lacking a signal sequence.

17. The method of claim 9, wherein the composition comprises the expression product of SEQ ID NO: 2.

* * * * *

SEQUENCE LISTING

```
<160> NUMBER OF SEQ ID NOS: 6

<210> SEQ ID NO 1
<211> LENGTH: 604
<212> TYPE: PRT
<213> ORGANISM: Homo sapiens

<400> SEQUENCE: 1
```

Met Met Arg Ala Val Trp Glu Ala Leu Ala Ala Leu Ala Ala Val Ala
1               5                   10                  15

Cys Leu Val Gly Ala Val Arg Gly Gly Pro Gly Leu Ser Met Phe Ala
                20                  25                  30

Gly Gln Ala Ala Gln Pro Asp Pro Cys Ser Asp Glu Asn Gly His Pro
            35                  40                  45

```
Arg Arg Cys Ile Pro Asp Phe Val Asn Ala Ala Phe Gly Lys Asp Val
    50                  55                  60

Arg Val Ser Ser Thr Cys Gly Arg Pro Ala Arg Tyr Cys Val Val
65                  70                  75                  80

Ser Glu Arg Gly Glu Arg Leu Arg Ser Cys His Leu Cys Asn Ala
                85                  90                  95

Ser Asp Pro Lys Lys Ala His Pro Pro Ala Phe Leu Thr Asp Leu Asn
            100                 105                 110

Asn Pro His Asn Leu Thr Cys Trp Gln Ser Glu Asn Tyr Leu Gln Phe
        115                 120                 125

Pro His Asn Val Thr Leu Thr Leu Ser Leu Gly Lys Lys Phe Glu Val
    130                 135                 140

Thr Tyr Val Ser Leu Gln Phe Cys Ser Pro Arg Pro Glu Ser Met Ala
145                 150                 155                 160

Ile Tyr Lys Ser Met Asp Tyr Gly Arg Thr Trp Val Pro Phe Gln Phe
                165                 170                 175

Tyr Ser Thr Gln Cys Arg Lys Met Tyr Asn Arg Pro His Arg Ala Pro
            180                 185                 190

Ile Thr Lys Gln Asn Glu Gln Glu Ala Val Cys Thr Asp Ser His Thr
        195                 200                 205

Asp Met Arg Pro Leu Ser Gly Gly Leu Ile Ala Phe Ser Thr Leu Asp
    210                 215                 220

Gly Arg Pro Ser Ala His Asp Phe Asp Asn Ser Pro Val Leu Gln Asp
225                 230                 235                 240

Trp Val Thr Ala Thr Asp Ile Arg Val Ala Phe Ser Arg Leu His Thr
                245                 250                 255

Phe Gly Asp Glu Asn Glu Asp Asp Ser Glu Leu Ala Arg Asp Ser Tyr
            260                 265                 270

Phe Tyr Ala Val Ser Asp Leu Gln Val Gly Gly Arg Cys Lys Cys Asn
        275                 280                 285

Gly His Ala Ala Arg Cys Val Arg Asp Arg Thr Asp Ser Leu Val Cys
    290                 295                 300

Asp Cys Arg His Asn Thr Ala Gly Pro Glu Cys Asp Arg Cys Lys Pro
305                 310                 315                 320

Phe His Tyr Asp Arg Pro Trp Gln Arg Ala Thr Ala Arg Glu Ala Asn
                325                 330                 335

Glu Cys Val Ala Cys Asn Cys Asn Leu His Ala Arg Arg Cys Arg Phe
            340                 345                 350

Asn Met Glu Leu Tyr Lys Leu Ser Gly Arg Lys Ser Gly Gly Val Cys
        355                 360                 365

Leu Asn Cys Arg His Asn Thr Ala Gly Arg His Cys His Tyr Cys Lys
    370                 375                 380

Glu Gly Tyr Tyr Arg Asp Met Gly Lys Pro Ile Thr His Arg Lys Ala
385                 390                 395                 400

Cys Lys Ala Cys Asp Cys His Pro Val Gly Ala Ala Gly Lys Thr Cys
                405                 410                 415

Asn Gln Thr Thr Gly Gln Cys Pro Cys Lys Asp Gly Val Thr Gly Ile
            420                 425                 430

Thr Cys Asn Arg Cys Ala Lys Gly Tyr Gln Gln Ser Arg Ser Pro Ile
        435                 440                 445

Ala Pro Cys Ile Lys Ile Pro Val Ala Pro Pro Thr Thr Ala Ala Ser
    450                 455                 460

Ser Val Glu Glu Pro Glu Asp Cys Asp Ser Tyr Cys Lys Ala Ser Lys
```

```
                                465                 470                 475                 480
                            Gly Lys Leu Lys Ile Asn Met Lys Lys Tyr Cys Lys Lys Asp Tyr Ala
                                                485                 490                 495

Val Gln Ile His Ile Leu Lys Ala Asp Lys Ala Gly Asp Trp Trp Lys
                                        500                 505                 510

Phe Thr Val Asn Ile Ile Ser Val Tyr Lys Gln Gly Thr Ser Arg Ile
                                        515                 520                 525

Arg Arg Gly Asp Gln Ser Leu Trp Ile Arg Ser Arg Asp Ile Ala Cys
                                    530                 535                 540

Lys Cys Pro Lys Ile Lys Pro Leu Lys Lys Tyr Leu Leu Leu Gly Asn
                            545                 550                 555                 560

Ala Glu Asp Ser Pro Asp Gln Ser Gly Ile Val Ala Asp Lys Ser Ser
                                            565                 570                 575

Leu Val Ile Gln Trp Arg Asp Thr Trp Ala Arg Arg Leu Arg Lys Phe
                                        580                 585                 590

Gln Gln Arg Glu Lys Lys Gly Lys Cys Lys Lys Ala
                                        595                 600

<210> SEQ ID NO 2
<211> LENGTH: 1989
<212> TYPE: DNA
<213> ORGANISM: Homo sapiens

<400> SEQUENCE: 2
agcttcgggg gcgagcgctc gtgtgtgtga gtgcgcgccg gccagcgcgc cttctgcggc      60
aggcggacag atcctcggcg cggcagggcc ggggcaagct ggacgcagca tgatgcgcgc     120
agtgtgggag gcgctggcgg cgctggcggc ggtggcgtgc ctggtgggcg cggtgcgcgg     180
cgggcccggg ctcagcatgt tcgcgggcca ggcggcgcag cccgatccct gctcggacga     240
gaacggccac ccgcgccgct gcatcccgga ctttgtcaat gcggccttcg gcaaggacgt     300
gcgcgtgtcc agcacctgcg gccggccccc ggcgcgctac tgcgtggtga gcgagcgcgg     360
cgaggagcgg ctgcgctcgt gccacctctg caacgcgtcc gaccccaaga aggcgcaccc     420
gcccgccttc ctcaccgacc tcaacaaccc gcacaacctg acgtgctggc agtccgagaa     480
ctacctgcag ttcccgcaca acgtcacgct cacactgtcc ctcggcaaga agttcgaagt     540
gacctacgtg agcctgcagt tctgctcgcc gcggcccgag tccatggcca tctacaagtc     600
catggactac gggcgcacgt gggtgcccct ccagttctac tccacgcagt gccgcaagat     660
gtacaaccgg ccgcaccgcg cgcccatcac caagcagaac gagcaggagg ccgtgtgcac     720
cgactcgcac accgacatgc gcccgctctc gggcggcctc atcgccttca gcacgctgga     780
cgggcggccc tcggcgcacg acttcgacaa ctcgcccgtg ctgcaggact gggtcacggc     840
cacagacatc cgcgtggcct tcagccgcct gcacacgttc ggcgacgaga cgaggacga     900 ctcggagctg gcgcgcgact cgtacttcta cgccgtgtcc gacctgcagg tgggcggccg     960
gtgcaagtgc aacggccacg cggcccgctg cgtgcgcgac cgcaccgaca gcctggtgtg    1020
cgactgcagg cacaacacgg ccggcccgga gtgcgaccgc tgcaagccct tccactacga    1080
ccggccctgg cagcgcgcca cagcccgcga agccaacgag tgcgtggcct gtaactgcaa    1140
cctgcatgcc cggcgctgcc gcttcaacat ggagctctac aagctttcgg ggcgcaagag    1200
cggaggtgtc tgcctcaact gtcgccacaa caccgccggc cgccactgcc attactgcaa    1260
ggagggctac taccgcgaca tgggcaagcc catcacccac cggaaggcct gcaaagcctg    1320
tgattgccac cctgtggggtg ctgctggcaa aacctgcaac caaaccaccg ccagtgtcc     1380
```

```
ctgcaaggac ggcgtgacgg gtatcacctg caaccgctgc gccaaaggct accagcagag    1440
ccgctctccc atcgccccct gcataaagat ccctgtagcg ccgccgacga ctgcagccag    1500
cagcgtggag gagcctgaag actgcgattc ctactgcaag gcctccaagg ggaagctgaa    1560
gattaacatg aaaaagtact gcaagaagga ctatgccgtc cagatccaca tcctgaaggc    1620
ggacaaggcg ggggactggt ggaagttcac ggtgaacatc atctccgtgt ataagcaggg    1680
cacgagccgc atccgccgcg gtgaccgag cctgtggatc cgctcgcggg acatcgcctg    1740
caagtgtccc aaaatcaagc ccctcaagaa gtacctgctg ctgggcaacg cggaggactc    1800
tccggaccag agcggcatcg tggccgataa aagcagcctg gtgatccagt ggcgggacac    1860
gtgggcgcgg cggctgcgca agttccagca gcgtgagaag aagggcaagt gcaagaaggc    1920
ctagcgccga ggcagcgggc gggcgggccg ggcgggcccg agggcggggc gagcgagacg    1980
gcgcttggc                                                           1989

<210> SEQ ID NO 3
<211> LENGTH: 24
<212> TYPE: DNA
<213> ORGANISM: Artificial sequence
<220> FEATURE:
<223> OTHER INFORMATION: chemically synthesized

<400> SEQUENCE: 3
caccatgttg gtgttctttg caga                                            24

<210> SEQ ID NO 4
<211> LENGTH: 21
<212> TYPE: DNA
<213> ORGANISM: Artificial sequence
<220> FEATURE:
<223> OTHER INFORMATION: chemically sythesized

<400> SEQUENCE: 4
ctagttctgc atctgctcaa a                                               21

<210> SEQ ID NO 5
<211> LENGTH: 33
<212> TYPE: DNA
<213> ORGANISM: Artificial sequence
<220> FEATURE:
<223> OTHER INFORMATION: chemically synthesized

<400> SEQUENCE: 5
gaggacttca gtctgtagag tagcagtgct ctc                                  33

<210> SEQ ID NO 6
<211> LENGTH: 33
<212> TYPE: DNA
<213> ORGANISM: Artificial sequence
<220> FEATURE:
<223> OTHER INFORMATION: chemically synthesized

<400> SEQUENCE: 6
gagagcactg ctactctaca gactgaagtc ctc                                  33
```